US010294451B2

(12) United States Patent
Geddes

(10) Patent No.: US 10,294,451 B2
(45) Date of Patent: May 21, 2019

(54) FLOW AND STATIC LYSING SYSTEMS AND METHODS FOR ULTRA-RAPID ISOLATION AND FRAGMENTATION OF BIOLOGICAL MATERIALS BY MICROWAVE IRRADIATION

(71) Applicant: Chris D. Geddes, Bel-Air, MD (US)

(72) Inventor: Chris D. Geddes, Bel-Air, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 506 days.

(21) Appl. No.: 15/134,691

(22) Filed: Apr. 21, 2016

(65) Prior Publication Data

US 2016/0312174 A1 Oct. 27, 2016

Related U.S. Application Data

(60) Provisional application No. 62/150,924, filed on Apr. 22, 2015.

(51) Int. Cl.
*B01L 3/00* (2006.01)
*G01N 33/553* (2006.01)
(Continued)

(52) U.S. Cl.
CPC ....... *C12M 47/06* (2013.01); *B01L 3/502707* (2013.01); *C12M 23/16* (2013.01);
(Continued)

(58) Field of Classification Search
CPC ......... B01L 2200/10; B01L 2400/0454; B01L 3/502707; B01L 7/52; C12M 23/16;
(Continued)

(56) References Cited

U.S. PATENT DOCUMENTS

| 4,662,969 A | 5/1987 | Wang et al. |
| 4,672,040 A | 6/1987 | Josephson |

(Continued)

FOREIGN PATENT DOCUMENTS

| WO | WO198909408 | 10/1989 |
| WO | WO2004024191 | 3/2004 |
| WO | WO2007095527 | 8/2007 |

OTHER PUBLICATIONS

Adak, G.K. et al. (2002) Trends in indigenous foodborne disease and deaths, England and Wales: 1992 to 2000. Gut 51: 832-841.

(Continued)

*Primary Examiner* — Jennifer Wecker
(74) *Attorney, Agent, or Firm* — Marianne Fuierer; Olive Law Group

(57) ABSTRACT

The present invention provides for lysing systems and methods to rapidly lyse bugs, bacteria, viruses, cells and/or algae in an efficient manner in addition to fragmenting DNA and/or RNA onto smaller pieces. Solutions or gases containing the biological material to be lysed are introduced or pumped (flow) between two or more apexes of metallic triangles with microwave energy focused at the apexes. Subsequently, the rapid heating of fluid between the apexes lyses cells allows for increased collection of the lysate, the inner genetic materials or other components for further purification or isolating thereafter.

25 Claims, 19 Drawing Sheets

Specification includes a Sequence Listing.

(51) Int. Cl.
- *C12M 1/00* (2006.01)
- *C12N 13/00* (2006.01)
- *C12N 15/10* (2006.01)
- *C12M 3/06* (2006.01)
- *C12N 1/06* (2006.01)
- *C12Q 1/68* (2018.01)
- *C12M 1/34* (2006.01)
- *C12Q 1/6816* (2018.01)
- *B01L 7/00* (2006.01)

(52) U.S. Cl.
CPC ............ *C12M 45/07* (2013.01); *C12N 1/066* (2013.01); *C12N 13/00* (2013.01); *G01N 33/553* (2013.01); *B01L 7/52* (2013.01); *B01L 2200/10* (2013.01); *B01L 2400/0454* (2013.01); *C12Q 1/6816* (2013.01)

(58) Field of Classification Search
CPC ....... C12M 45/07; C12M 47/06; C12N 13/00; C12N 1/066; G01N 33/553; C12Q 1/6816
See application file for complete search history.

(56) References Cited

U.S. PATENT DOCUMENTS

| | | | |
|---|---|---|---|
| 4,735,778 A | 4/1988 | Maruyama et al. | |
| 5,017,009 A | 5/1991 | Schutt et al. | |
| 5,049,434 A | 9/1991 | Wasulko | |
| 5,449,918 A | 9/1995 | Krull et al. | |
| 5,766,953 A | 6/1998 | Kennedy | |
| 5,779,976 A | 7/1998 | Leland et al. | |
| 5,780,249 A | 7/1998 | Wang et al. | |
| 5,866,433 A | 2/1999 | Schalkhammer et al. | |
| 6,066,448 A | 5/2000 | Wohlstadter et al. | |
| 6,140,045 A | 10/2000 | Wohlstadter et al. | |
| 6,329,209 B1 | 12/2001 | Wagner et al. | |
| 6,362,011 B1 | 3/2002 | Massey et al. | |
| 7,095,502 B2 | 8/2006 | Lakowicz et al. | |
| 7,253,452 B2 | 8/2007 | Steckel et al. | |
| 7,348,182 B2 | 3/2008 | Martin et al. | |
| 7,351,590 B2 | 4/2008 | Martin | |
| 7,400,397 B2 | 7/2008 | Lakowicz et al. | |
| 7,564,546 B2 | 7/2009 | Maier et al. | |
| 7,566,783 B2 | 7/2009 | Lakowicz | |
| 7,718,445 B2 | 5/2010 | Martin | |
| 7,718,804 B2 | 5/2010 | Geddes et al. | |
| 7,732,215 B2 | 6/2010 | Geddes et al. | |
| 7,776,528 B2 | 8/2010 | Lakowicz | |
| 7,939,333 B2 | 5/2011 | Geddes et al. | |
| 7,989,220 B2 | 8/2011 | Lakowicz et al. | |
| 8,008,067 B2 | 8/2011 | Geddes et al. | |
| 8,027,039 B2 | 9/2011 | Lakowicz et al. | |
| 8,034,633 B2 | 10/2011 | Geddes | |
| 8,075,956 B2 | 12/2011 | Geddes et al. | |
| 8,101,424 B2 | 1/2012 | Geddes | |
| 8,114,598 B2 | 2/2012 | Geddes et al. | |
| 8,182,878 B2 | 5/2012 | Geddes et al. | |
| 8,318,087 B2 | 11/2012 | Geddes | |
| 8,338,602 B2 | 12/2012 | Geddes et al. | |
| 8,404,450 B2 | 3/2013 | Geddes et al. | |
| 8,569,502 B2 | 10/2013 | Geddes et al. | |
| 8,618,505 B2 | 12/2013 | Geddes | |
| 8,679,402 B2 | 3/2014 | Geddes | |
| 8,679,855 B2 | 3/2014 | Geddes | |
| 8,722,428 B2* | 5/2014 | Geddes ............... | G01N 21/6408 436/525 |
| 8,735,175 B2 | 5/2014 | Geddes | |
| 8,759,110 B2 | 6/2014 | Geddes | |
| 9,075,018 B2 | 7/2015 | Geddes et al. | |
| 9,170,197 B2 | 10/2015 | Geddes et al. | |
| 2003/0228682 A1 | 12/2003 | Lakowicz | |
| 2004/0038388 A1 | 2/2004 | Yamamoto et al. | |
| 2005/0244977 A1 | 11/2005 | Drachev et al. | |
| 2006/0256331 A1 | 11/2006 | Geddes | |
| 2007/0269826 A1 | 11/2007 | Geddes | |
| 2008/0215122 A1 | 9/2008 | Geddes | |
| 2009/0022766 A1 | 1/2009 | Geddes | |
| 2009/0325199 A1 | 12/2009 | Geddes | |
| 2010/0003695 A1* | 1/2010 | Geddes ................. | G01N 21/76 435/7.1 |
| 2011/0020946 A1 | 1/2011 | Geddes | |
| 2011/0081655 A1* | 4/2011 | Narahara ............. | G01N 21/648 435/6.12 |
| 2011/0207236 A1 | 8/2011 | Geddes | |
| 2012/0021443 A1 | 1/2012 | Geddes | |
| 2012/0028270 A1 | 2/2012 | Geddes | |
| 2012/0107952 A1 | 5/2012 | Geddes | |
| 2012/0282630 A1 | 11/2012 | Geddes | |
| 2013/0115710 A1 | 5/2013 | Geddes | |
| 2013/0156938 A1 | 6/2013 | Geddes | |

OTHER PUBLICATIONS

Ali, A. et al. (2009) Multiplex PCR for differential diagnosis of emerging typhoidal pathogens directly from blood samples. Epidemiol Infect 137: 102-107.

Almeida, C. et al. (2010) Fluorescence in situ hybridization method using a peptide nucleic acid probe for identification of *Salmonella* spp. in a broad spectrum of samples. Appl Environ Microbiol 76: 4476-4485.

"APHL/CDC Panel Summary Reports, Laboratory Diagnostic Testing for Chlamydia trachomatis and Neisseria gonorrhoeae, and Laboratory Diagnostic Testing for Treponema pallidum. 2009. Guidelines for the Laboratory Testing of STDs. http://www.aphl.org/aphlprograms/infectious/std/Pages/stdtestingg uidelines.aspx."

Aslan, K. et al. (2005) Microwave-accelerated metal-enhanced fluorescence: Platform technology for ultrafast and ultrabright assays. Analytical Chemistry, vol. 77, pp. 8057-8067.

Aslan, K. et al. (2005) Annealed silver-island films for ap, plications in metal-enhanced fluorescence: interpretation in terms of radiating plasmons. J Fluoresc 15: 643-654.

Aslan, K. et al. (2006) Microwave-Accelerated Metal-Enhanced Fluorescence (MAMEF) with silver colloids in 96-well plates: Application to ultra fast and sensitive immunoassays, High Throughput Screening and drug discovery. Journal of Immunological Methods, vol. 312, pp. 137-147.

Aslan, K. et al. (2006) Microwave Accelerated and Metal Enhanced Fluorescence Myoglobin Detection on Silvered Surfaces: Potential Application to Myocardial Infarction Diagnosis,' Plasmonics, vol. 1, pp. 53-59.

Aslan, K. et al. (2006) Microwave-accelerated Metal-enhanced Fluorescence (MAMEF): Application to ultra fast and sensitive clinical assays. Journal of Fluorescence, vol. 16, pp. 3-8.

Aslan, K. et al. (2007) Microwave-accelerated metal-enhanced fluorescence: an ultra-fast and sensitive DNA sensing platform. Analyst, vol. 132, pp. 1122-1129.

Aslan, K. et al. (2007) Microwave-accelerated metal-enhanced fluorescence: application to detection of genomic and exosporium anthrax DNA in <30 seconds. Analyst, vol. 132, pp. 1130-1138.

Aslan, K. et al. (2008) New tools for rapid clinical and bioagent diagnostics: microwaves and plasmonic nanostructures. Analyst 133: 1469-1480.

Aslan, K. et al. (2008) Extraction and detection of DNA from *Bacillus anthracis* spores and the vegetative cells within 1 min. Anal Chem 80: 4125-4132.

Aslan, K. et al. (2008) A review of an ultrafast and sensitive bioassay platform technology: Microwave-accelerated metal-enhanced fluorescence. Plasmonics 3: 89-101.

Berkley, J.A. et al. (2005) Bacteremia among children admitted to a rural hospital in Kenya. N Engl J Med 352: 39-47.

Brent, A.J. et al. (2006) *Salmonella* bacteremia in Kenyan children. Pediatr Infect Dis J 25: 230-236.

Centers for Disease Control and Prevention, sexually transmitted disease surveillance, 2008. Atlanta, GA: U.S. Department of Health and Human Services, CDC., 2010.

(56) References Cited

OTHER PUBLICATIONS

Durmaz, G. et al. (2003) Optimum detection times for bacteria and yeast species with the BACTEC 9120 aerobic blood culture system: evaluation for a 5-year period in a Turkish university hospital. J Clin Microbiol 41: 819-821.
Frankel, G. (1994) Detection of *Salmonella typhi* by PCR. J Clin Microbiol 32: 1415.
Gaydos, C. A. et al. (2003) J. Schachter, 'Performance of the APTIMA Combo 2 assay for the multiplex detection of Chlamydia trachomatis and Neisseria gonorrheae in female urine and endocervical swab specimens.,' J Clin Microbiol vol. 304, pp. 304-309.
Gradel, K.O. et al. (2006) Incidence and prognosis of non-typhoid *Salmonella* bacteraemia in Denmark: a 10-year county-based follow-up study. Eur J Clin Microbiol Infect Dis 25: 151-158.
Graham, S.M. et al. (2000) Clinical presentation of non-typhoidal *Salmonella* bacteraemia in Malawian children. Trans R Soc Trop Med Hyg 94: 310-314.
Graham, S.M. et al. (2000) Nontyphoidal *Salmonella* infections of children in tropical Africa. Pediatr Infect Dis J 19: 1189-1196.
Hague, A. et al. (2001) Utility of PCR in diagnosis of problematic cases of typhoid. Jpn J Infect Dis 54: 237-239.
Hatta, M. et al. (2007) Detection of *Salmonella typhi* by nested polymerase chain reaction in blood, urine, and stool samples. Am J Trop Med Hyg 76: 139-143.
Hill, P.C. et al. (2007) Bacteraemia in patients admitted to an urban hospital in West Africa. BMC Infect Dis 7: 2.
Huppert, J. et al. (2010) What's the point? How point-of-care sexually transmitted infection tests can impact infected patients., Point of Care, vol. 9, pp. 36-46.
Ikumapayi, U.N. et al. (2007) Molecular epidemiology of community-acquired invasive non-typhoidal *Salmonella* among children aged 2-29 months in rural Gambia and discovery of a new serovar, *Salmonella enterica* Dingiri. J Med Microbiol 56: 1479-1484.
Jones, T.F. et al. (2008) Salmonellosis outcomes differ substantially by serotype. J Infect Dis 198: 109-114.
Kariuki, S. et al. (2006) Characterisation of community acquired non-typhoidal *Salmonella* from bacteraemia and diarrhoeal infections in children admitted to hospital in Nairobi, Kenya. BMC Microbiol 6: 101.
Kennedy, M. et al. (2004) Hospitalizations and deaths due to *Salmonella* infections, FoodNet, 1996-1999. Clin Infect Dis 38 Suppl 3: S142-S148.
Kumar, A. et al. (2002) Detection of *Salmonella typhi* by polymerase chain reaction: implications in diagnosis of typhoid fever. Infect Genet Evol 2: 107-110.
Lehmann, L.E. et al. (2008) A multiplex real-time PCR assay for rapid detection and differentiation of 25 bacterial and fungal pathogens from whole blood samples. Med Microbiol Immunol 197: 313-324.
Lepage, P. et al. (1987) Community-acquired bacteraemia in African children. Lancet 1: 1458-1461.
Levy, H. et al. (2008) PCR method to identify *Salmonella enterica* serovars Typhi, Paratyphi A, and Paratyphi B among *Salmonella* isolates from the blood of patients with clinical enteric fever. J Clin Microbiol 46: 1861-1866.
Malorny, B. et al. (2008) Enumeration of *Salmonella* bacteria in food and feed samples by real-time PCR for quantitative microbial risk assessment. Appl Environ Microbiol 74: 1299-1304.
Mancini, N. et al. (2008) Molecular diagnosis of sepsis in neutropenic patients with haematological malignancies. J Med Microbiol 57: 601-604.
Mandomando, I. et al. (2009) Invasive non-typhoidal *Salmonella* in Mozambican children. Trop Med Int Health 14: 1467-1474.
Massi, M.N. et al. (2003) Rapid diagnosis of typhoid fever by PCR assay using one pair of primers from flagellin gene of *Salmonella typhi*. J Infect Chemother 9: 233-237.
Nga, T.V. et al. (2010) The sensitivity of real-time PCR amplification targeting invasive *Salmonella* serovars in biological specimens. BMC Infect Dis 10: 125.

O'Dempsey, T.J. et al. (1994) Importance of enteric bacteria as a cause of pneumonia, meningitis and septicemia among children in a rural community in The Gambia, West Africa. Pediatr Infect Dis J 13: 122-128.
Paolucci, M. et al. (2009) Laboratory diagnosis of late-onset sepsis in newborns by multiplex real-time PCR. J Med Microbiol 58: 533-534.
Papaevangelou, V. et al. (2004) *Salmonella* bacteraemia in a tertiary children's hospital. Scand J Infect Dis 36: 547-551.
Prakash, P. et al. (2005) Evaluation of nested PCR in diagnosis of typhoid fever. J Clin Microbiol 43: 431-432.
Pribik, R. et al. (2009) Metal-Enhanced Fluorescence (MEF): Physical characterization of silver Island Films and exploring sample geometries. Chemical Physics Letters, vol. 478, pp. 70-74.
Reisner, B.S. et al. (1999) Times to detection of bacteria and yeasts in BACTEC 9240 blood culture bottles. J Clin Microbiol 37: 2024-2026.
Sanchez-Jimenez, M.M. et al. (2004) Validation of a PCR for diagnosis of typhoid fever and salmonellosis by amplification of the *hilA* gene in clinical samples from Colombian patients. J Med Microbiol 53: 875-878.
Schuck, P.J. et al. Improving the mismatch between light and nanoscale objects with gold bowtie nanoantennas. Jan. 2005, Phys Rev Letters, 94: pp. 017402-1-017402-4.
Song, J.H. et al. (1993) Detection of *Salmonella typhi* in the blood of patients with typhoid fever by polymerase chain reaction. J Clin Microbiol 31: 1439-1443.
Tennant, S.M. et al. (2010) Identification by PCR of non-typhoidal *Salmonella enterica* serovars associated with invasive infections among febrile patients in Mali. PLoS Negl Trop Dis 4: e621.
Threlfall, E.J. et al. (1992) *Salmonella* bacteraemia in England and Wales, 1981-1990. J Clin Pathol 45: 34-36.
Van Der Pol, D. F. B. et al. (2001) Multicenter evaluation of the BDProbeTec ET system for the detection of Chalmydia trachomatis and Neisseria gonorrhoeae in urine specimens, female endocervical swabs, and male urethral swabs. J Clin Microbiol, vol. 39, pp. 1008-1016.
Vaughan, O.P.H. et al. (2006) Direct Observation of Surface-Mediated Thioacetyl Deprotection: Covalent Tethering of a Thiol-Terminated Porphyrin to the Ag(100) Surface, J. Am. Chem. Soc., vol. 128, pp. 9578-9579.
Voetsch, A.C. et al. (2004) FoodNet estimate of the burden of illness caused by nontyphoidal *Salmonella* infections in the United States. Clin Infect Dis 38 Suppl 3: S127-S134.
Vugia, D.J. et al. (2004) Invasive *Salmonella* infections in the United States, FoodNet, 1996-1999: incidence, serotype distribution, and outcome. Clin Infect Dis 38 Suppl 3: S149-S156.
Wain, J. et al. (1998) Quantitation of bacteria in blood of typhoid fever patients and relationship between counts and clinical features, transmissibility, and antibiotic resistance. J Clin Microbiol 36: 1683-1687.
Wain, J. et al. (2001) Quantitation of bacteria in bone marrow from patients with typhoid fever: relationship between counts and clinical features. J Clin Microbiol 39: 1571-1576.
Wain, J et al. (2008) The laboratory diagnosis of enteric fever. J Infect Developing Countries 2: 421-425.
Walsh, A.L. et al. (2000) Bacteremia in febrile Malawian children: clinical and microbiologic features. Pediatr Infect Dis J 19: 312-318.
Woods, D.F. et al. (2008) Rapid multiplex PCR and real-time TaqMan PCR assays for detection of *Salmonella enterica* and the highly virulent serovars Choleraesuis and Paratyphi C. J Clin Microbiol 46: 4018-4022.
Zhang, Jian et al. (2004) First observation of surface plasmon-coupled electrochemiluminescence,, Chemical Physics Letters, vol. 393, No. 4-6: 483-487.
Zhang, Y. et al. (2010) Development of a Microwave—Accelerated Metal-Enhanced Fluorescence 40 second, 100 cfu/mL Point of Care Assay for the Detection of *Chlamydia trachomatis*. IEEE Trans Biomed Eng.

(56) References Cited

OTHER PUBLICATIONS

Zhou, L. et al. (2010) A fast and highly sensitive blood culture PCR method for clinical detection of *Salmonella enterica* serovar Typhi. Ann Clin Microbiol. Antimicrob 9: 14.

* cited by examiner

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial Sequence
```

```
<220> FEATURE:
<223> OTHER INFORMATION: Synthetic Construct

<400> SEQUENCE: 1
tggagcatgt ggtttaattc ga                                               22

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
tgcgggactt aacccaaca                                                   19

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
acaggtgctg catggctgtc gtcagct                                          27

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4
tctccggagg attccgcaca tgtcaaaa                                         28

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
aagggaaagc tctgtctcca gagtggtcaa                                       30
```

FLOW AND STATIC LYSING SYSTEMS AND METHODS FOR ULTRA-RAPID ISOLATION AND FRAGMENTATION OF BIOLOGICAL MATERIALS BY MICROWAVE IRRADIATION

CROSS-REFERENCE TO RELATED APPLICATIONS

This application claims priority to U.S. Provisional Application No. 62/150,924 filed on Apr. 22, 2015, the content of which is incorporated by reference herein for all purposes.

FIELD OF INVENTION

The present invention is directed to a system and method for lysing and/or fragmenting biological materials, such as bugs, bacteria, viruses, cells and/or algae using microwave power in combination with bow-tie structures thereby forming a reaction area to enhance lysing efficiency.

BACKGROUND OF THE INVENTION

Bacterial infections are a major health problem worldwide and rapid detection is critical for disease management and prognosis. Molecular approaches are faster and in most cases, more sensitive than culture-based approaches for identification of the infection-causing organism(s). The use of PCR-based approaches for detection of bacterial pathogens has significantly increased over the last two decades primarily due to its ease of use and sensitivity. Nevertheless, there is a continued need for the development of faster, more sensitive, and cheaper molecular approaches. Microwave-accelerated metal-enhanced fluorescence (MAMEF) assays have shown promise as an analytical assay for the detection of bacterial pathogens.[1-6]. MAMEF is an amplification-free hybridization assay which combines the benefits of metal-enhanced fluorescence to increase assay sensitivity with low power microwaves to accelerate biological recognition events.[7] The increased sensitivity of the assay is underpinned by the enhancement of fluorescence emission in the near-field resulting from the non-radiative transfer of energy from the excited fluorophore to silver nanoparticles. The use of low-power microwaves reduces the assay run time by up to several 1000 fold, which when combined with enhanced fluorescence provides for a powerful platform for ultra-rapid and sensitive bioassays. [8-9]

One of the critical technical aspects of MAMEF is the requirement of small DNA fragment for DNA hybridization. While a variety of approaches including nebulization, mechanical and acoustic shearing, and ultrasonic baths can be used to generate DNA fragments of tunable sizes (100 bp-8 kb), these approaches require sophisticated instrumentation.[10]

Sample preparation (lysis) is key to the development of many clinical point-of-care (POC) and laboratory tests involving cellular genetic analysis. Nucleic acid isolation is a significant bottleneck in Polymerase Chain Reaction (PCR)-based approaches, and requires many cumbersome, lengthy and costly steps. Additionally, commercially-available lysis kits are expensive and different protocols are required for different biological matrices.

Microwave irradiation has been primarily used for sterilization purposes, but most recently it has been used for other purposes including acceleration of chemical reactions and isolation of genomic DNA. Microwaves have been shown to be effective for the isolation of genomic DNA from a variety of biological systems including bacteria [11-12], bacteriophage [13], spores [5], but also for preparation of DNA for real-time PCR analysis.[14] More recently, microwave irradiation has been used exclusively for the purpose of DNA fragmentation for various molecular approaches. Yang and Hang have recently reported on the use of microwave irradiation to generate DNA fragments for next-generation DNA applications.[14] Although successful, their microwave irradiation procedure requires a specialized instrument, it is time-consuming and adjusting the power and irradiation time can introduce issues such as overheating and loss of volume.

To address such shortcomings and complexities, it would be advantageous to develop a system and method to rapidly lyse biological material, such as bacterial cells, to isolate specific materials.

SUMMARY OF THE INVENTION

The present invention provides for lysing systems and methods to rapidly lyse bugs, bacteria, viruses, cells and/or algae in an efficient manner in addition to fragmenting DNA and/or RNA onto smaller pieces. Solutions or gases containing the biological material to be lysed are introduced or pumped (flow) between two or more apexes of triangles with microwave energy focused at the apexes. Subsequently, the rapid heating of fluid between the apexes lysing cells allows for increased collection of the lysate, the inner genetic materials or other components for further purification or isolating thereafter.

In one aspect, the present invention provides for a system for lysing and fragmenting a biological material comprising:
  a substrate;
  a reaction vessel recessed into the substrate or positioned on the substrate;
  at least a first and second metallic triangle arranged in the bottom of the reaction vessel wherein an apex of the first metallic triangle is opposite an apex of second metallic triangle to form a reaction zone positioned between the first and second metallic triangle; and
  a source of microwave energy positioned and focused to emit microwave energy and deliver to the reaction zone an amount of microwave energy to lyse and/or fragment the biological material.

In another aspect the present invention provides for a microfluidic system for lysing and fragmenting a biological material comprising:
  a substrate;
  at least a first and second metallic triangle positioned on the substrate wherein an apex of the first metallic triangle is opposite an apex of second metallic triangle to form a reaction zone positioned between the first and second metallic triangle;
  a layer of polymeric material covering at least the first and second metallic triangles and the reaction zone;
  a source of microwave energy positioned and focused to emit microwave energy and deliver to the reaction zone an amount of microwave energy to lyse and/or fragment the biological material;
  an inlet channel recessed into the polymeric layer and communicatively connected to the reaction zone and of a sufficient size to provide flow of a solution of the biological material through the reaction zone; and
  an outlet channel or collection vessel communicatively connected to the reaction zone for collection or movement of the lysed or fragmented biological material from the reaction zone.

The above system can be fabricated to be a closed loop system wherein both the inlet and outlet are connected to a pumping system to provide for a continuous flow of biological material between the apexes. Further by adjusting the heating time, microwave energy and flow rate of the solution or gas through the heating apexes, the lysing efficiency can be adjusted. Such a closed system provides for the ability to capture and transport dangerous gases, side products or released biologicals before, during and after lysing. Importantly, the flow of biological material through the reaction zone, formed between the apexes of the triangular structures, provides for non-physical contact of the flow of the biological material with the metallic triangular structures. Such non-physical contact provides for the reuse of the system.

In yet another aspect, the present invention provides for a method to isolate DNA or RNA from bacteria, viruses, yeast, algae, or any microorganism. The DNA and/or RNA is released from the microorganism by lysing with the application of a low-power microwave based approach utilizing centimeter-sized metallic disjointed "bow-tie" structures to focus the microwaves into a lysing volume. A 5 s to 180 s focused microwave burst, preferably about 30 s to 100 s, is sufficient to induce morphological changes in a microorganism.

The bow-tie structures, made of two triangles, which are deposited on the substrate, may be fabricated from a metallic material including silver, gold, copper, zinc, indium, rhodium, aluminum, or platinum wherein the metallic material is formed into a patterned shape. Preferably, the patterned shape includes geometric shapes having at least one apex, such as, a triangle, square, rectangle, trapezoid and/or combinations thereof, wherein the numerous apexes are adjacent to each other, thereby creating a reactive zone therebetween. The reactive zone may have a diameter or distance between the adjacent and/or opposing apexes ranging from about 0.01 μm to 5 cm and more preferably from about 0.5 mm to 30 mm, and more preferably from about 1 mm to 15 mm. Further, the reactive zone can be positioned on assay system with multiple wells wherein the reactive zone is within the wells and exposure to microwave energy causes lysing of included microorganism and/or enhances the reactions therein.

The triangular metallic structure may be right triangles, equilateral triangles, isosceles triangles, scalene triangles, obtuse triangles and/or acute triangles and preferably equilateral triangles ranging in size from about 6 mm to 25 mm and more preferably in a range from 10 mm to 16 mm.

The substrate may be fabricated of a polymeric material, glass, paper, nitrocellulose, combinations thereof or any material that provides sufficient stability for placement of the metallic material. Preferably a polymeric material such as polydimethylsiloxane is used which has the ability to increase E-field intensity.

Further, the apex area/reactive zone is exposed to microwave energy in an amount to cause lysing of cellular material; increase the reaction rate in biological interactions and enhance electric fields by focusing electromagnetic fields in the reactive zone.

Yet another aspect of the present invention provides for a method for lysing and fragmenting a biological material, the method comprising:
  introducing the biological material into a reaction vessel, wherein at least a first and second metallic triangle is arranged on a bottom surface of the reaction vessel wherein an apex of the first metallic triangle is opposite an apex of second metallic triangle to form a reaction zone positioned between the first and second metallic triangle; and
  applying and focusing microwave energy to the reaction zone in an amount to lyse and/or fragment the biological material.

A still further aspect of the present invention provides for a method for lysing and fragmenting a biological material, the method comprising:
  introducing the biological material through an inlet opening and a channel to pass through a reaction zone, wherein the reaction zone is positioned between an apex of a first metallic triangle and an apex of a second metallic triangle; and
  applying and focusing microwave energy to the reaction zone in an amount to lyse and/or fragment the biological material and optionally providing a pumping system to move the biological material from the inlet opening through channel and the reactive zone and any formed lysate to a collection vessel.

A further aspect of the present invention, relates to a kit for lysing and/or fragmenting biological material, the kit comprising:
  a reaction vessel comprising a layer of triangular shaped immobilized metal particles deposited in the reaction vessel, wherein the triangular metal particles are in a patterned shape of a bow-tie wherein the apexes of two triangles are arranged in alignment and forming a reactive zone.

Another aspect of the present invention, relates to a kit for lysing and/or fragmenting biological material, the kit comprising:
  a surface substrate comprising a layer of triangular shaped immobilized metal particles deposited on the surface substrate, wherein the triangular metal particles are in a patterned shape of a bow-tie wherein the apexes of two triangles are arranged in alignment and forming a reactive zone; and
  a polymeric layer positioned over at least the two triangles and reactive zone wherein the polymeric layer comprises an inlet opening and a connecting channel of sufficient length to move biological material from the inlet opening to pass through the reactive zone to a collection vessel or an outlet opening.

Other aspects and advantages of the invention will be more fully apparent from the ensuing disclosure and appended claims.

DETAILED DESCRIPTION OF THE INVENTION

Figure 1:
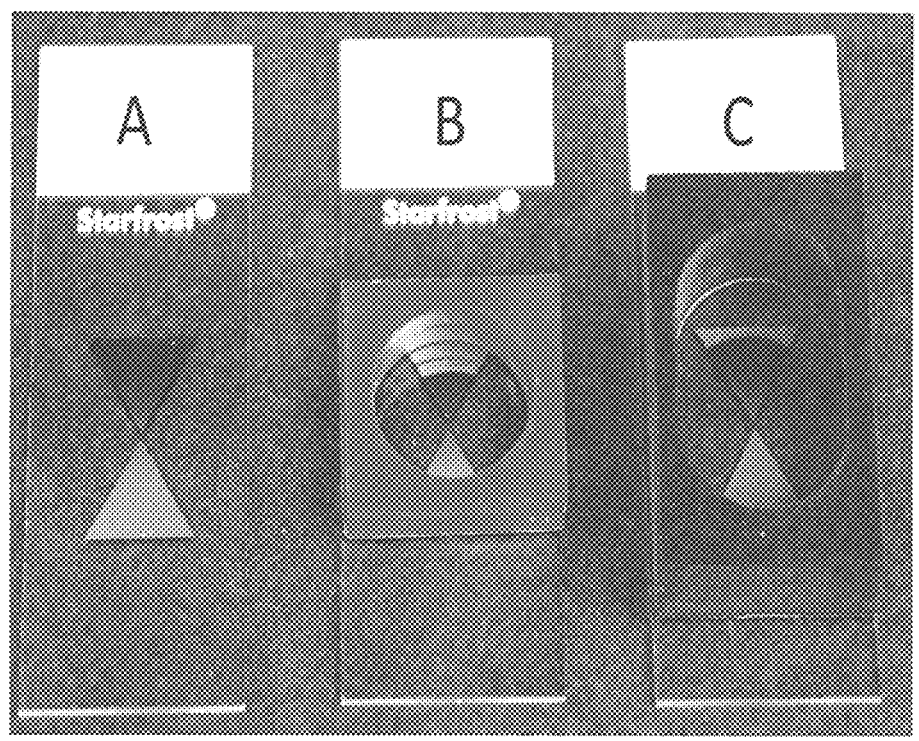
FIG. 1 shows (A) Bow-tie disjointed gold triangle deposited on glass slides. (B) Lysing chamber with small isolator (500 μL to 1 mL), (C) Lysing chamber with large isolator (up to 2 mL volume).

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

In the present invention, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. Importantly, molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field.

In the present invention, microwave radiation may be provided by an electromagnetic source having a frequency in a range between 0.3 and 10 GHz, more preferably from about 1 GHz to 4 GHz, and a power level in a range between about 10 mwatts and 1000 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy for not only the lysing process but also to provide energy to excite fluorescing molecules. The energy can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron.

Clearly, the level of microwave energy is sufficiently high to cause lysing of cell tissue during the lysing process, with a range of power levels between 100 watts to 600 watts and then can be adjusted to a lower energy level for the detection assay, that being between 30 mwatts to about 100 watts to cause an increase in the kinetics of the hybridization reaction without causing damage to any biological materials in the assay system.

Bacterial DNA may be isolated using various DNA isolation methods known in the art. A kit suitable for isolating DNA is the Roche High Pure PCR Template Preparation Kit. DNA concentration is estimated by measuring the absorbance of a solution at 260 nm. An $A_{260}$ value of 1 is equivalent to a DNA concentration of 50 µg/ml for double stranded DNA and 20 µg/ml for single-stranded DNA. The purity of a sample is assessed by calculating the 260/280 nm absorbance ratio. This is approximately a ratio greater than 1.5 for protein-free DNA samples.

Oligonucleotide sequences should be examined to ensure that the nucleotide sequence does not contain self-complementary stretches that could potentially form stem loops. Complementarities between oligonucleotide pairs are also avoided as this can lead to formation of primer-dimer artifacts. Binding of the oligomer to other regions of the template DNA is avoided by prior comparison of the DNA nucleotide sequence of the template DNA to be amplified for local high percentage match to the primer, using the PRIMER EXPRESS software package from Perkin Elmer ABI. The step of washing the assay surface after target capture will remove any non-hybridized complimentary labeled capture stands if the background fluorescence signal levels from the bulk solution are high.

The assays of the present invention may include a single substrate or a first and second substrate with transference of products from the first to the second substrate after the lysing process. The single substrate may comprise multiple triangular metallic structures with apexes forming a reactive zone between the apexes which may be used in both the lysing and detection processes. Alternatively the first substrate includes the metallic triangles and the second surface comprises silver colloids or islands wherein the first substrate is used in the lysing process and the second substrate used in the assay for detecting the DNA of a target pathogen.

Deposition of Gold Triangle on Glass Substrates to Lyse *Salmonella*.

Glass microwave slides were covered with a mask (12.3 mm in size with a 1 mm gap between two triangles), leaving a triangle bowtie region exposed. Equilateral gold triangles of 12.3 mm were subsequently deposited onto glass microscope slides through the mask using a BOC Edwards 306 vacuum deposition with vacuum $3.0 \times 10^{-6}$ Torr, with a deposition rate of ~1 A/s. Two layers of self-adhesive silicon isolators (D 2.5 mm) were placed on top of the Au bow-tie region to create a sample well, directly over the BowTie apexes.

The present invention provides for rapidly lysing bacterial cells, isolate and fragment microbial DNA using highly-focused microwave radiation. Two organisms with different cellular membrane architecture, *Neisseria gonorrhoeae* and *Listeria morrocytogenes* have been chosen as model organisms. Subsequently, it is shown herein that highly focused microwaves at 2.45 GHz, using 12.3 mm gold film equilateral triangles, are able to rapidly lyse both bacteria and fragment DNA. When compared to traditional heating, microwave radiation is more rapid (under 90 seconds) and effective for DNA fragmentation. Different lysing conditions are required for lysing *L. monocytogenes* than for *N. gonorrhoeae*. Overall, the extent of DNA fragmentation is proportional to microwave radiation time and power thus allowing for this simple lysing approach to be used with molecular detection platforms.

The present invention focuses microwaves and is also based on the use of bow-tie structures in the form of two equilateral gold triangles deposited on a glass microscope slide. However, contrary to light-focusing antennas, these bow-ties structures are not nanometer scale but in fact cm-scale, consistent with the much longer wavelength of microwaves, that being, ~12.3 cm. The use of a silicone isolator over the bow-tie structures creates a chamber capable of holding a specific volume of sample while the bow-tie structures help focus the microwaves onto the sample thus increasing lysing efficiency, through rapid water heating, both within and outside the organism to be lysed.

In the present invention, the effects of various experimental parameters such as microwave power, time and chamber size on culture survival and DNA fragmentation are described. Furthermore, the efficiency of highly-focused microwave lysing to conventional heating is compared. Two pathogens, *Neisseria gonorrhoeae* and *Listeria monocytogenes*, have been selected as experimental models due to their clinical relevance and differing cell wall architectures. *Gonorrhea* is the second most prevalent sexually-transmitted infection (STI) reported to the Centers for Disease Control and prevention (CDC).[15] *Listeria monocytogenes*, a gram positive pathogen, is a major cause of foodborne illnesses.[16] The use of these two different pathogens allows the study of the fundamental mechanism of microbial lysing and DNA fragmentation by microwave irradiation and to determine if a single microwave-based lysing protocol could be used to lyse bacteria with different cell composition.

Methods

Microwave Lysing Using Bow-Tie Geometries

Gold bow-tie geometries (FIG. 1A), with highly focus microwaves at 2.45 GHz onto samples in a sample chamber used for lysing which is the equivalent of a low cost commercial low-power microwave ovens for with only a few slight modifications inside for sample mounting. The simulations allow us to determine the spatial and temporal profile of the focused microwaves to optimize the heating effects. The rapid heating of the water (both around and within the organism) rapidly disrupts cellular membranes. [6-7]

Bacterial Strains

*Neisseria gonorrhoeae* (ATCC 43069) and *Listeria monocytogenes* (ATCC 4428) were obtained from ATCC (Manassas, Va.). Bacterial dilutions ($10^8$ CFU/mL and lower) were prepared from overnight cultures in distilled, autoclaved water and submitted to lysing by conventional heating and microwaves as described below.

Deposition of Gold Triangles on Glass Substrates on Lysing Chambers

Equilateral gold (99.999%) triangles of 12.3 mm and about 100 nm thicknesses (FIG. 1) were deposited onto glass microscope slides using a BOC Edwards 306 vacuum deposition unit at a rate 0.1 nm/s. Following the deposition of gold triangles in a bow-tie structure configuration, self-adhesive isolators were placed over the triangles to create a lysing chamber. Briefly, two layers of silicon isolators with a diameter of 20 mm were placed on top of the bow-tie region to create a chamber for lysing sample volumes from 500 µL to 1 mL (FIG. 1B). For lysing larger volumes (1 mL to 2 mL), a single silicon black isolator (D=32 mm) was used to create a lysing chamber (FIG. 1C).

Lysis of *N. gonorrhoeae* and *L. monocytogenes* Using Microwave Irradiation

Fresh dilutions ($10^8$ CFU/mL) of *N. gonorrhoeae* and *L. monocytogenes* were lysed in the aforementioned lysing chambers with and without bow-tie lysing structures. The small lysing chambers (FIG. 1B) were used to lyse sample volumes of 500 µL and 1 mL. Sample volumes of 1 mL were also lysed in the large isolators (FIG. 1C) as well as samples with 2 mL sample volume. All samples were exposed to 2.45 GHz microwave irradiation in a 900-watt microwave for either 30, 60 or 90 seconds. The bacterial suspensions were exposed to three different microwave powers; 10%, 30%, and 50% corresponding to 90, 270, and 450 W, over the entire microwave cavity. The temperature of the samples was recorded prior to lysing and after each experimental condition (i.e. 10% power for 30 seconds, etc.). Immediately following microwave irradiation, a 20 µL aliquot of each lysate was plated on selective media, and incubated overnight at 37° C.

Lysis of *N. gonorrhoeae* and *L. monocytogenes* by Conventional Heating

Microbial cells were lysed by heating 4 mL of bacterial suspensions ($10^8$ CFU/mL) in sterile scintillation vials fitted with a thermometer for temperature monitoring. Bacterial suspensions were heated to 40° C., 50° C., 60° C. and 70° C. for 30, 60, or 90 seconds. These temperatures were selected to simulate temperatures reached during microwave irradiation. To determine culture survival, a 20 μL aliquot of each lysate was plated on selective media and incubated overnight at 37° C.

Analysis of DNA Fragmentation by Gel Electrophoresis

Prior to gel electrophoresis, the DNA was ethanol precipitated with 0.1× volume of 3 M sodium acetate pH 5.2 and 2× volume of pre-chilled molecular grade ethanol, followed by centrifugation. Samples were centrifuged at 14000 rpm for 20 minutes, and the supernatant discarded. DNA pellets were air-dried and re-hydrated in 200 μL of DNA rehydration solution (Promega, Madison, Wis.). To determine DNA fragmentation pattern, 40 μL of each sample was electrophoresed on 1.5% agarose gel in the presence of ethidium bromide.

Real-Time PCR Analysis

Prior to PCR analysis, all samples were centrifuged at 8000 rpm for 10 minutes to separate cells from DNA. The supernatant was used for PCR analysis using a previously described PCR assay. [18-23] Real-time PCR was performed using a 16S PCR. Briefly, each PCR reaction was performed in a total volume of 50 μl, utilizing 30 μl of PCR master mix and 20 μl of sample. PCR master mix contained 25 μl of 2× Taqman universal PCR mix (PE Applied Biosystems, Foster City, Calif.), 1.5 μl of 67 μM forward primer (p891: 5'TGGAGCATGTGGTTTAATTCGA3') (SEQ ID NO: 1) and reverse primer (p1033: 5'TGCGGGACTTAACCCAACA3') (SEQ ID NO: 2) 1 μl of 2.5 units of Amplitaq Gold (PE Applied Biosystems, Foster City, Calif.) and 1 μl of 10 μM probe were added to make up the final master mix before sample was added. Taqman probes for gram negative bacteria, *Neisseria gonnorrhoae*, and *Listeria monocytogenes* were used where appropriate with sequences as follows: Gram Negative: 5 'VIC-ACAGGTGCTGCATGGCTGTCGTCAGCT-MGBNFQ3' (SEQ ID NO: 3) *Neisseria gonnorrhoae*: 5'6FAM-TCTCCGGAGGATTCCGCACATGTCAAAA-MGBNFQ3' (SEQ ID NO: 4), *Listeria monocytogenes*: 5'TET-AAGGGAAAGCTCTGTCTCCAGAGTGGTCAA-MGBNFQ3' (SEQ ID NO: 5). PCR was performed with an ABI 7900 HT sequence detection system (PE Applied Biosystems, Foster City, Calif.) with the following cycling conditions: preincubation at 50° C. for 2 min, denaturation at 95° C. for 10 min, and 50 repeats at 95° C. for 15 s, annealing/extension temperature at 60° C. for 60 s.

Results

Determination of Bacterial Load for DNA Fragmentation Analysis

Figure 2:
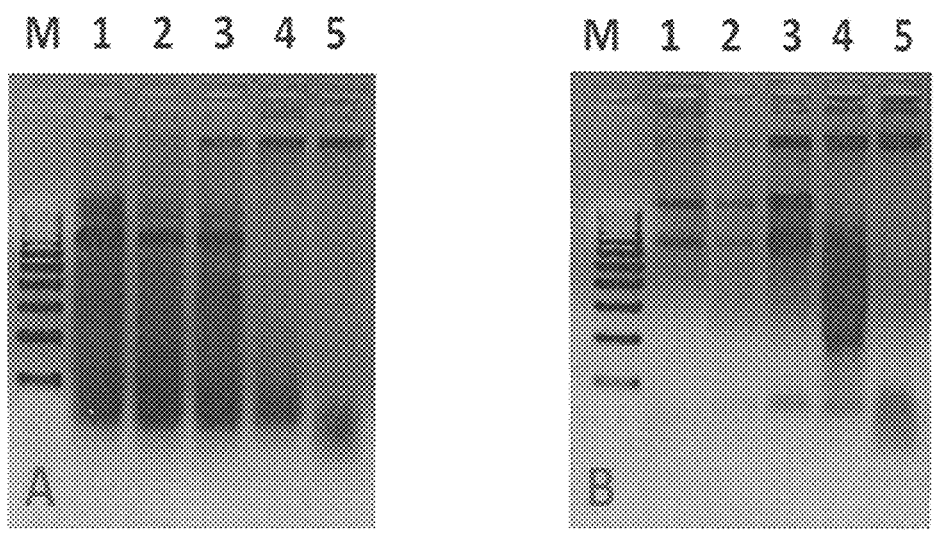
FIG. 2 shows DNA fragmentation pattern of (A) *Neisseria gonorrhoeae* and (B) *Listeria monocytogenes* suspension ($10^8$ CFU/mL) by boiling. M=100 bp DNA ladder; 1=Prelyse sample; 2=40° C.; 3=50° C.; 4=60° C.; 5=70° C.
Figure 8:
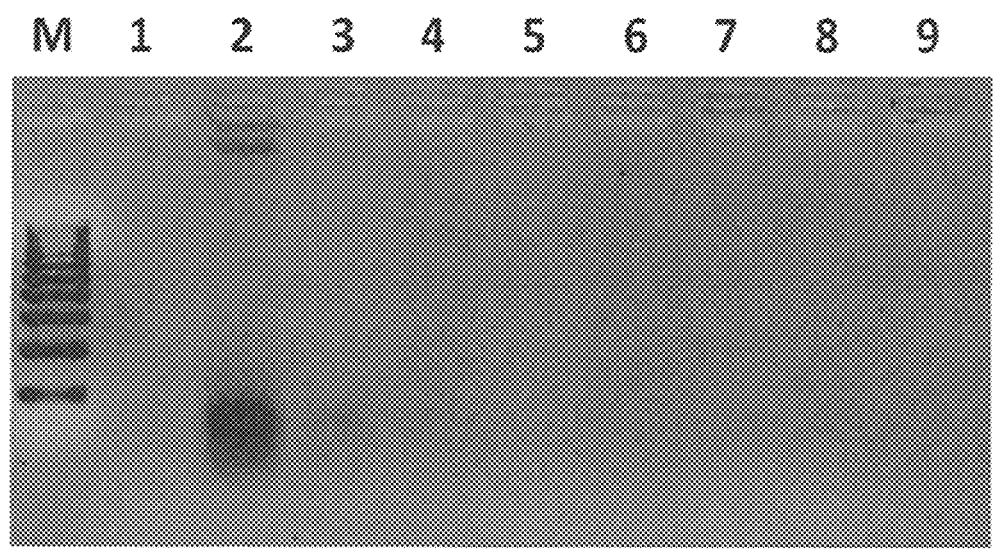
FIG. 8 shows lysing of *Neisseria gonorrhoeae* at different concentrations. M=100 bp DNA ladder; $10^6$ unlysed sample (Lane 1); $10^8$ lysed at 30% power—30 seconds (Lane 2); $10^6$ boiled for 60 seconds at 40° C. (Lane 3); 50° C. (Lane 4); 40° C. (Lane 5); 70° C. (Lane 6); $10^6$ microwave lysed at 30% power for 30 seconds (Lane 7); 60 second (lane 8); 90 seconds (Lane 9). Concentrations expressed as CFU/mL.

To determine the ideal bacterial concentration to evaluate DNA fragmentation patterns, serial dilutions of *Neisseria gonorrhoeae* were lysed by conventional heating (boiling) at temperatures ranging from 40° C.-70° C. and by microwave irradiation for 60 seconds at 270 W over the entire microwave cavity. As shown in FIGS. 2 and 8, $10^8$ CFU/mL was an ideal concentration for DNA fragmentation analysis. While culture survival could be determined by culturing suspensions of lower concentrations (data not shown), DNA fragments were not detected in samples with concentration less than $10^8$ CFU/mL (FIG. 8).

Effect of Conventional Heating on Culture Survival and DNA Fragmentation

Figure 3:
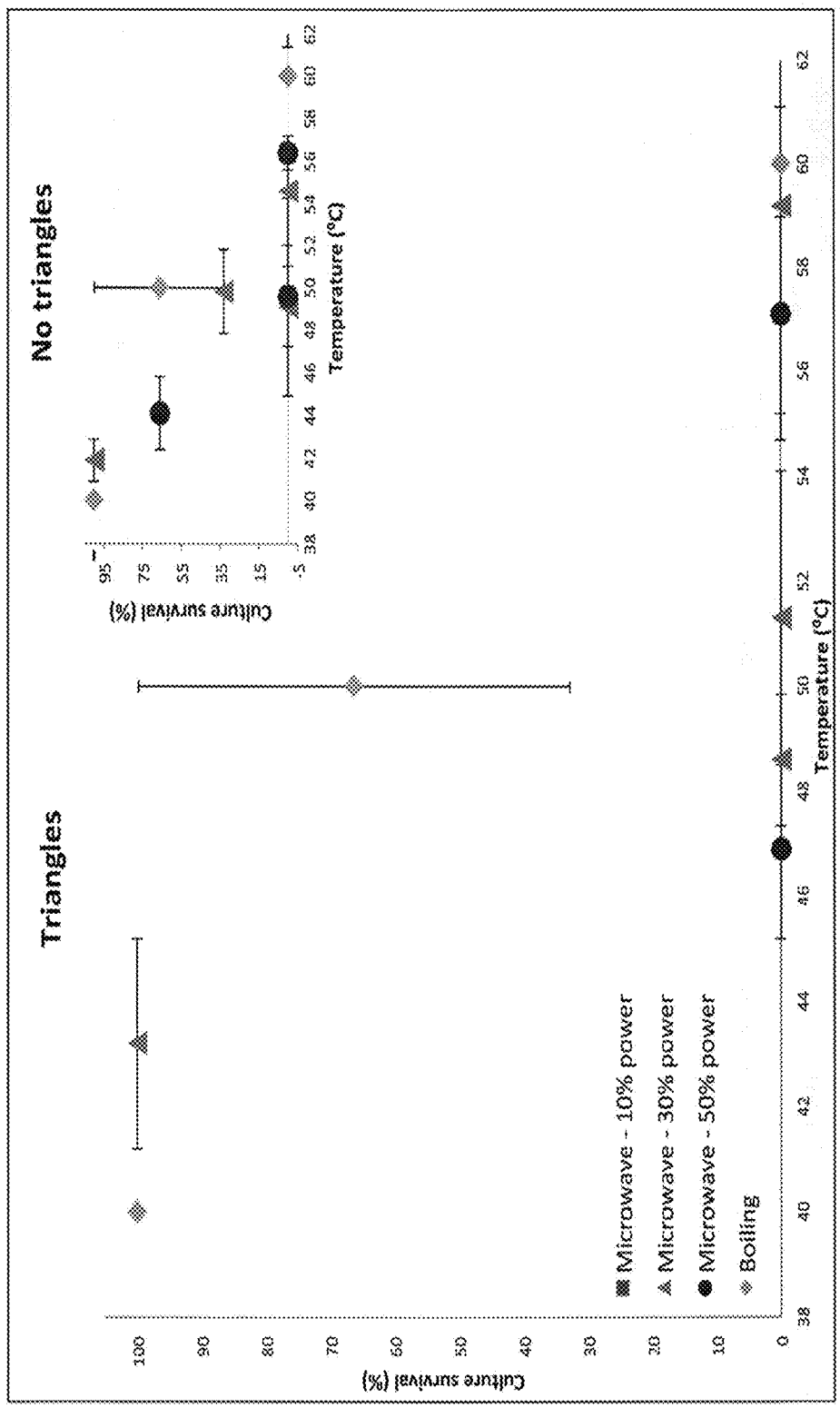
FIG. 3 shows survival of *Neisseria gonorrhoeae* vs. temperature.
Figure 4:
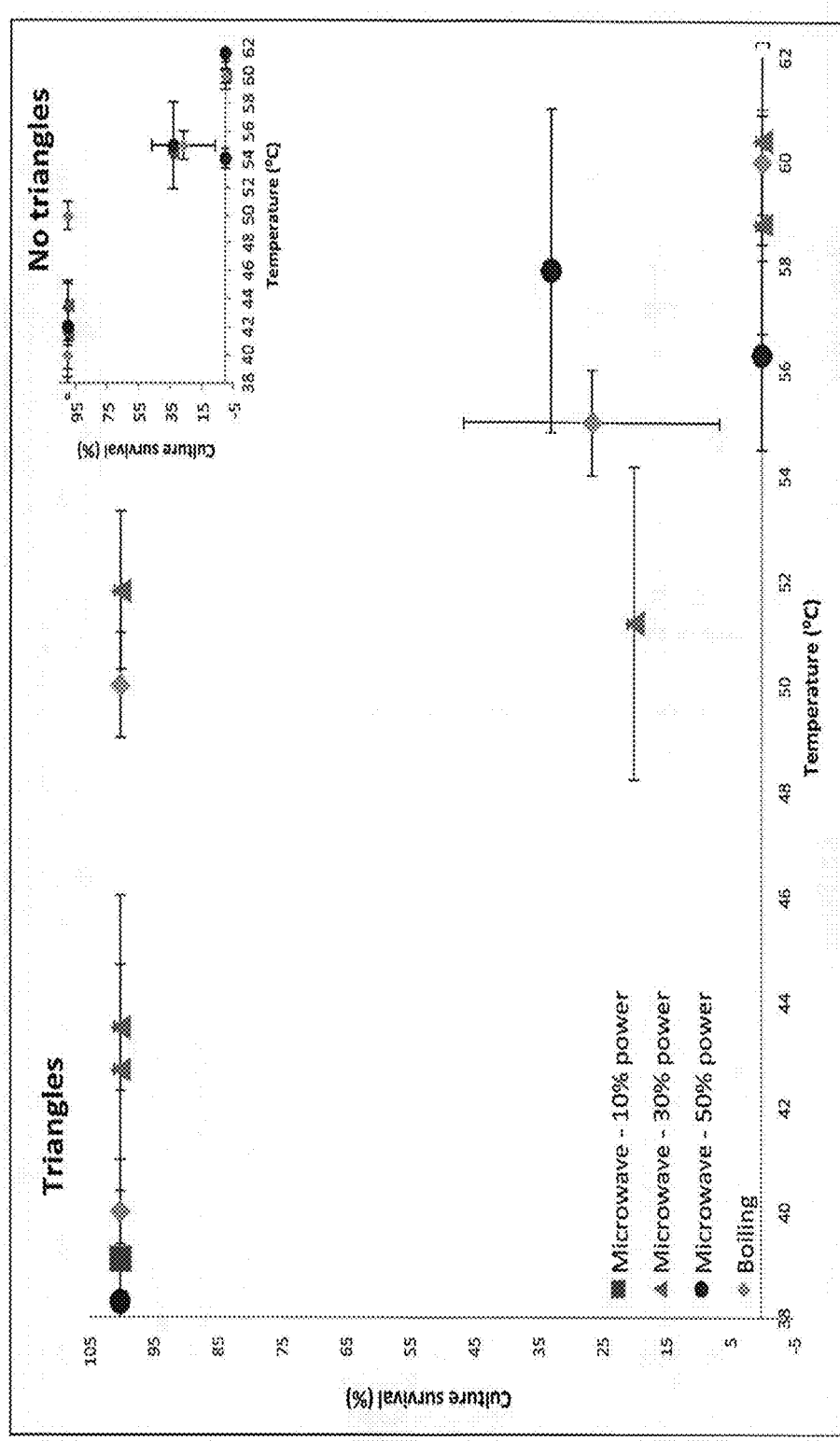
FIG. 4 shows survival of *Listeria monocytogenes* vs. temperature.

The temperatures (40°-70° C.) used for the conventional heating experiments were selected because the temperatures were similar to those reached by cultures following microwave irradiation (FIGS. 3 and 4). Overall, complete inactivation of *L. monocytogenes* cells by heating required higher temperatures than inactivation of *N. gonorrhoeae* cells (FIGS. 3 and 4). At 40° C., culture survival rates for either bacterial species were not affected. When the temperature reaches 50° C., a small and variable decrease in culture survival rates is observed for *N. gonorrhoeae* (FIG. 3), but not for *L. monocytogenes* (FIG. 4). Increasing the temperature of the culture to 55° C. significantly decreases the culture survival rates of *L. monocytogenes* (FIG. 4), and both bacterial organisms are inactivated when a temperature of 60° C. is reached (FIGS. 3 and 4). Similarly, higher temperatures result in increased DNA extraction and fragmentation. In the case of *N. gonorrhoeae* (FIG. 2A), extraction of high molecular weight (MW) genomic DNA increases when the temperature of the solution reaches 60° C. and complete fragmentation of low MW (700 to 1100 bps) DNA fragments is achieved. In the case of *L. monocytogenes*, partial DNA fragmentation is achieved at 60° C., but a significant amount of high MW DNA remains unfragmented even at 70° C. (FIG. 2B).

Effect of Microwaves and Temperature on Culture Survival

In order to evaluate the effects of heating by microwaves on culture survival, temperature readings were collected following microwave irradiation and the culture survival results compared to those by conventional heating at different temperatures (40°, 50°, 60° and 70° C.). Exposure of *N. gonorrhoeae* and *L. monocytogenes* cultures to low-power microwaves (10%) resulted in low culture temperatures and did not affect culture survival rates (FIGS. 3 and 4). However, exposing the cultures to higher microwave power resulted in decreased culture survival rates in a power- and temperature-dependent manner (FIGS. 3 and 4). When exposed to microwaves, the *N. gonorrhoeae* cultures were destroyed when the temperature of the cultures reached 46° C. (FIG. 3), while *L. monocytogenes* cultures were not killed until culture temperatures reached 54° C. (FIG. 4). Overall, culture survival rates were more significantly affected by microwaves than by conventional heating when culture survival rates between the two methods were compared at the same temperature. For example, *N. gonorrhoeae* cultures were completely killed when the temperature reached 46° C. by microwave heating while at temperatures of 50° C. only 35% of cultures were killed when exposed to conventional heating (FIG. 3). Similarly, 80% of *L. monocytogenes* cells were killed when exposed to microwaves and the temperature reached 51° C. while temperatures of 55° C. were required to kill the same proportion of *Listeria* cells when they were exposed to conventional heating (FIG. 4).

Effect of Microwaves on DNA Fragmentation

*Neisseria gonorrhoeae*

Figure 5:
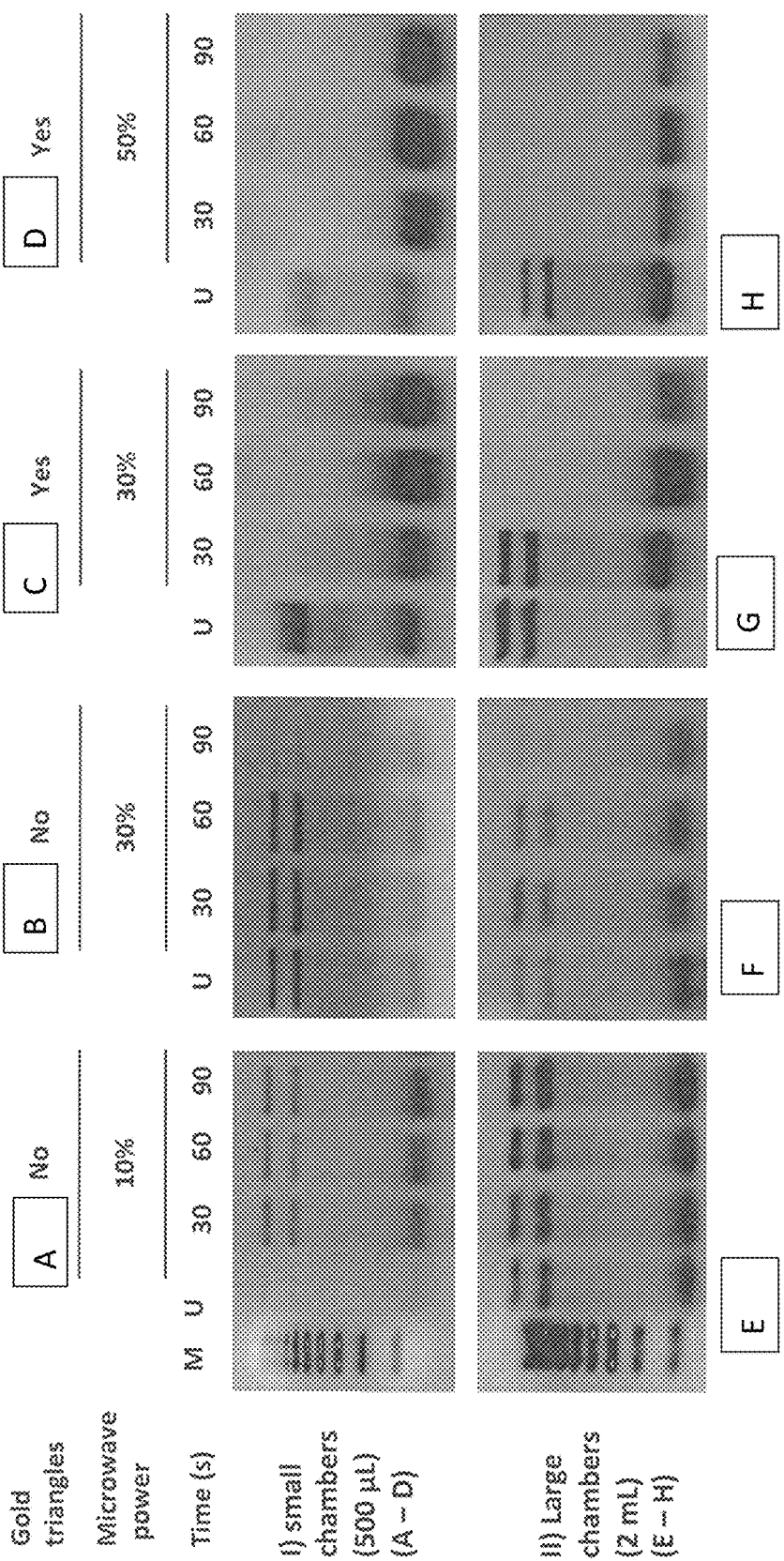
FIG. 5 shows DNA fragmentation pattern of *Neisseria gonorrhoeae* by microwave irradiation. (I) (A-D) 500 μL lysing volumes using small isolators. (II) (E-H) 2 ml lysing volumes using large isolators. M—100 bp DNA Marker; U—unlysed sample.

The use of low power microwaves (10%=90 W over the entire cavity) and a short exposure time (30 seconds) did not have a significant effect on DNA isolation (FIGS. 5A and B). However, the use of a bigger lysing chambers combined with longer exposure times (60 and 90 seconds) resulted in greater DNA isolation when compared to the 30 seconds exposure time or the pre-lyse sample (FIG. 5B), but did not result in DNA fragmentation. Increasing the microwave power to 30% and 50% (270 W or 450 W) resulted in the fragmentation of genomic DNA into fragments less than 100 bps (FIGS. 5C and D and 5G and H). At the highest microwave power investigated (50%=450 W), complete DNA fragmentation occurs regardless of exposure time (FIGS. 5D and H).

Effect of Microwaves on DNA Fragmentation

*Listeria monocytogenes*

Figure 6:
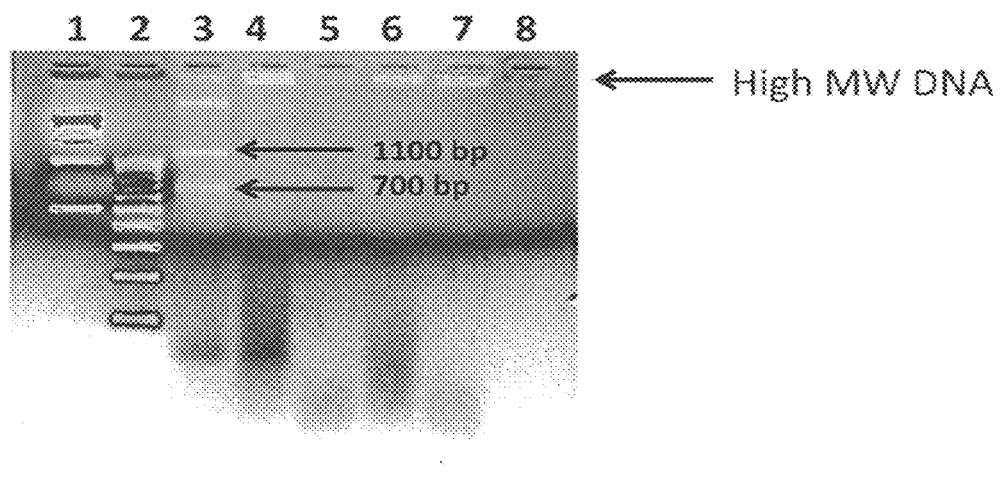
FIG. 6 shows DNA fragmentation pattern of *Listeria monocytogenes* by microwave irradiation. 1=500 bp DNA ladder; 2=100 bp DNA ladder; 3=Prelyse; 4=30% power—60 seconds; 5=50% power—90 seconds; 6=50% power—30 seconds; 7=50% power—60 seconds; 8=50% power—45 seconds (lysed twice. MW=molecular weight.

Attempts to lyse *L. monocytogenes* using experimental conditions that were used for lysing *N. gonorrhoeae* (30% power for 60 seconds) were not successful. As shown in FIG. 6 (lane 4), microwave irradiation at 30% power for 60 seconds resulted in the extraction of high MW DNA, and fragmentation of low MW DNA (700-1100 bps bands), but not to the degree observed for *N. gonorrhoeae* (FIG. 5C). Increasing the microwave power to 50% results in partial DNA fragmentation when the culture were microwave irradiated for 30 seconds (FIG. 6—Lane 6), while exposing the culture to longer microwave periods of 60 and 90 seconds results in very small DNA fragments (FIG. 6—Lanes 5 and 7). Furthermore, lysing the culture twice results in complete destruction of all of genomic DNA (Lane 8).

Effect of Microwave Focusing with Gold Triangles

*Neisseria gonorrhoeae*

It was investigated as how the use of bow-tie gold triangles deposited on glass slide (FIG. 1) might help to enhance lysing efficiency by focusing microwaves onto the lysing volume. At lower microwave power (10%=90 W), very little DNA fragmentation occurs regardless of whether or not the lysing triangles are used (FIGS. 5A and E), and data not shown. When cultures are exposed to microwave irradiation at 30% power (270 W) in the presence of lysing triangles, complete DNA fragmentation occurs in as little as 30 seconds (FIG. 5C). In the absence of lysing triangles, no DNA fragmentation is observed (FIG. 5B). The same enhancement of DNA fragmentation by lysing triangles is observed when the large lysing chambers (FIG. 1C) are used (FIG. 5G) in comparison to when the lysing chambers are omitted (FIG. 5F).

Effect of Lysing Geometry on DNA Fragmentation

*Neisseria gonorrhoeae*

To further elucidate the mechanism of bow-tie structures-based microwave focusing on DNA fragmentation, cultures were microwave irradiated in two chambers with different lysing geometries. It is theorized that the bulk of the microwave-driven energy is initially concentrated at the apex of the triangles resulting in the preferential lysing of cells near that location. When comparing cultures microwave irradiated in the presence of lysing triangles (FIGS. 5C-D and 5G-H), the amount of fragmented DNA is greater is cultures that were lysed with the small lysing chambers (FIG. 5C-D) than those lysed in the large lysing chambers (FIG. 5G-H). Overall, the use of the small lysing chambers in which the entire sample volume is directly above the lysing triangles (FIG. 1B) is more efficient for DNA fragmentation (FIGS. 5C and D) than when larger lysing chambers (FIG. 1C) are used at the same experimental conditions (FIGS. 5G and H). The difference in DNA fragmentation efficiency observed when using the small and large lysing chamber is not related to sample volume as there was no difference in fragmentation efficiency between lysing 1 or 2 mL of sample when using the larger lysing chamber (data not shown).

Effect of Microwave Lysing on PCR

Figure 7:
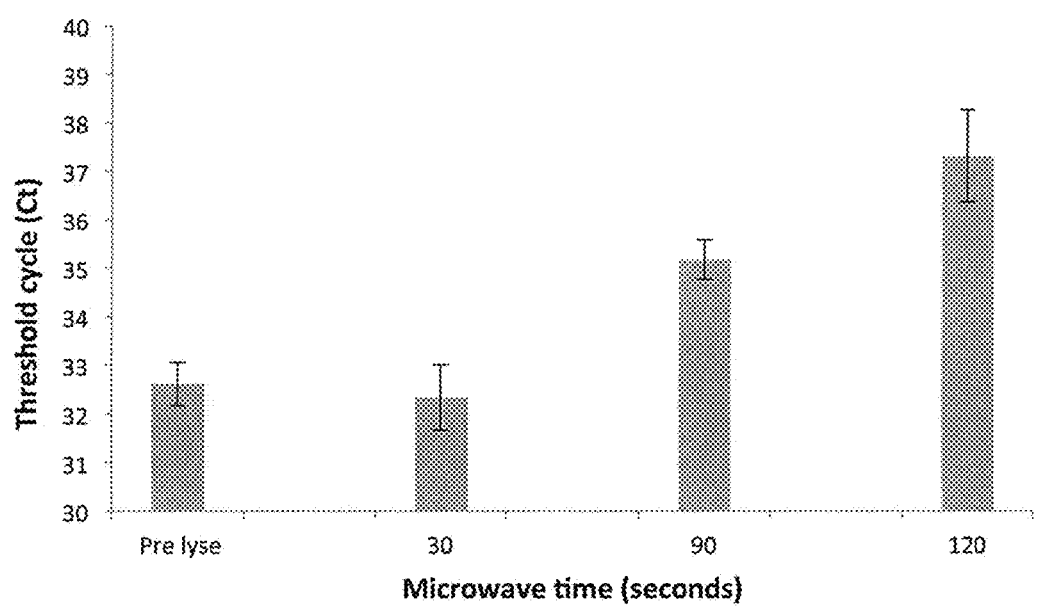
FIG. 7 shows detection of *Neisseria gonorrhoeae* by PCR before and after microwave irradiation at 30% power.

In order to show that microwave irradiation results in DNA fragmentation, pre- and post-microwave irradiation lysates of *N. gonorrhoeae* were tested by PCR. Exposure of *N. gonorrhoeae* to microwaves for 30 seconds does not affect the concentration of DNA template available for PCR. However, increasing the exposure time to 90 and 120 seconds increases the Threshold cycle (Ct) of the PCR reactions suggestive of a decrease in the concentration of template DNA available for PCR (FIG. 7).

Discussion

Isolation of DNA for molecular detection and gene expression assays is a time-consuming and often labor-extensive and expensive process. In order to improve on some of the shortcomings of current DNA extraction methodologies, the present invention demonstrates the potential utility of a microwave-based system for the rapid extraction and fragmentation of bacterial DNA. The goal is to show that the same lysing conditions may be used to two organisms with different cell wall structures, *Neisseria gonorrhoeae* and *Listeria monocytogenes*. While the results presented herein suggest that different (albeit only slightly different) conditions are necessary for the lysing of these two pathogens, there are several notable features about microwave-based lysing including: I) speed, II) lack of specialized instrumentation, Ill) cost, and IV) applicable to a variety of molecular methodologies due to its DNA fragmentation capacity.

Although commercially-available kits can be used for the isolation of bacterial DNA, they require a combination of thermal and enzymatic reactions resulting in long and labor-intensive procedures. The procedure set forth herein involving a 2.45 GHz household microwave can lyse gram-positive and gram-negative in as little as 60 seconds. As demonstrated by the present invention, the isolated DNA can then be successfully used for a variety of molecular approaches including PCR [24-25], MAMEF [1-6] and next generation sequencing.[14] Another notable feature of the presently disclosed microwave-based lysing system is the ability to simultaneously isolate and fragment genomic DNA. The DNA fragmentation patterns obtained from using the present system are similar to previous reported microwave studies [13-14], but without the need of a sophisticated microwave system, and yet still carried out in seconds instead of several minutes.

In addition to demonstrating the utility of a microwave-based lysing approach, one of the objectives of the present invention was to show how the use of bow-tie structures can be used for focusing microwaves and can enhance cell lysis and DNA fragmentation. Culture results for both *Gonorrhea* and *Listeria* suggest that not only are microwaves more effective that conventional heating to destroy bacterial cells, but that the additional of bow-tie structures to the lysing chambers leads to a decrease in cell survival and an increase in DNA fragmentation, at least for *Neisseria gonorrhea*. The superior efficacy of small lysing chambers over larger chambers for lysing and DNA fragmentation is likely attributable to the electric field distribution at the gap of the bow-tie geometries per unit lysing volume. Notably, during microwave irradiation there is a rapid increase in heating rate for solutions in close proximity to the gap of the 12.3 mm disjoined bow-tie structures. In the case of the small lysing chambers, the entire sample is located directly above the bow-tie structures and in closer proximity to the gap of the disjoined lysing triangles than when larger lysing chambers are used (FIGS. 1B and 1C).

With regards to developing a single microwave-based lysing protocol, the results shown herein suggest that gram-negative organism like *N. gonorrhoeae* can be successfully lysed and its DNA fragmented in under one minute. However, gram-positive organisms or hard-to-lyse organisms like *Listeria* might require a different protocol, which will likely require additional microwave power or increased exposure time. These results are supported by a previous study which suggests that following microwave irradiation there is a differential damage in bacterial cells on the basis of cell wall structure.[26] In order to successfully fragment Listerial DNA, temperatures higher that 70° C. might be required as suggested by the DNA fragmentation patterns obtained following conventional heating of *Listeria* culture at 70° C. Notably, microwave irradiation of *Listeria* cultures using the previously described parameters almost never reached 70° C. Furthermore, the use of disjoined bow-tie structures helps to enhance lysing and DNA fragmentation efficiency by focusing microwaves directly onto the sample.

Another aspect of the present invention provides for a flow lysing system and approach to rapidly lyse bugs, bacteria, viruses, cells or algae very efficiently. Solutions or gases containing the material to be lysed are pumped (flow) between two or more apexes, which focus microwaves at the apexes. Subsequently, the rapid heating of fluid between the apexes lyses cells, allowing for the near 100% efficient collection of the lysate, the inner genetic materials or other components sort after.

Figure 9:
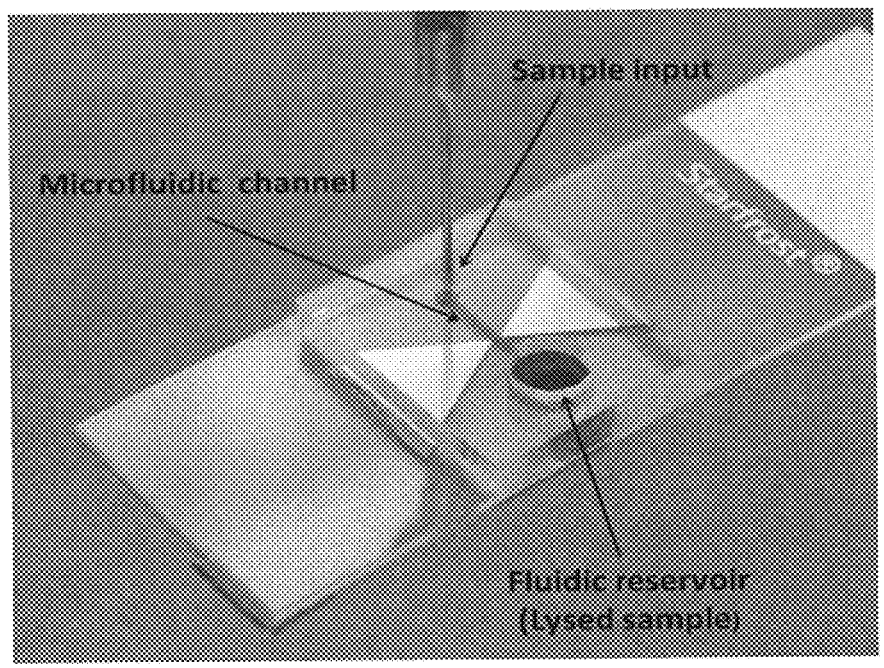
FIG. 9 shows a preferred system of the present invention showing the microfluidic channel and reaction zone comprising two equilateral triangles and formed between the apexes of the triangles.
Figure 19:
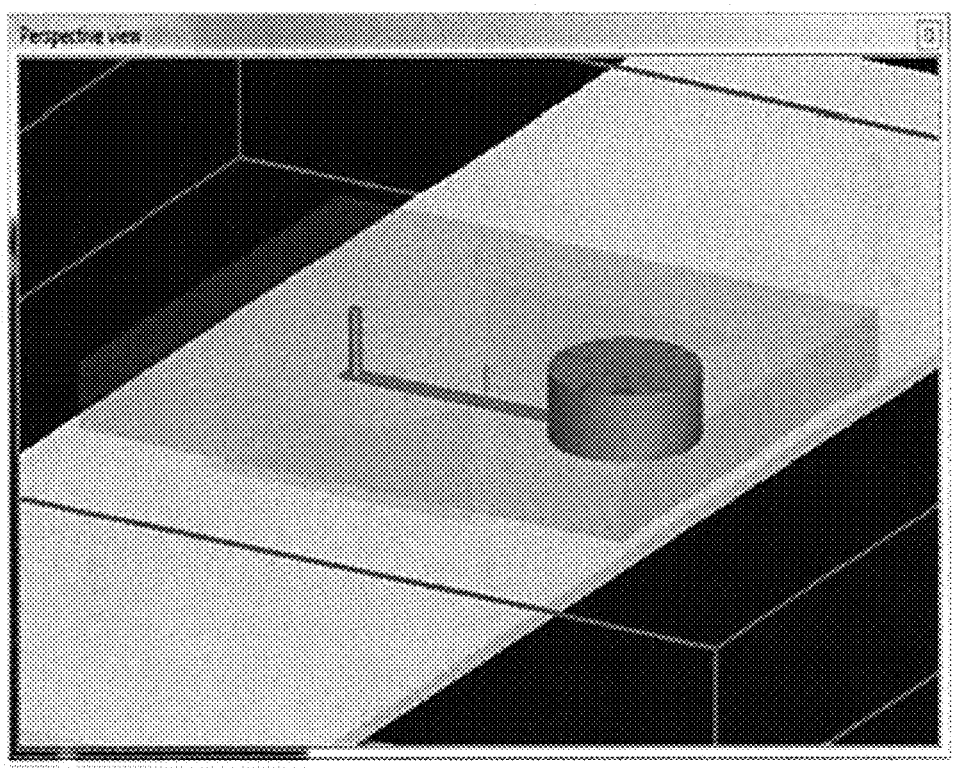
FIG. 19 shows a prospective view of the system shown in FIG. 9

A preferred embodiment is shown in FIG. 9 wherein a channel is constructed between the gold bow tie apexes in plastic materials to allow the material to flow between the triangles. In this figure, a red dye was added to show the channel visually. Both sides of the flow groove can be connected to a peristaltic pump for flow lysing. FIG. 19 provides a prospective view wherein the fluidic reservoir is a collection site for the lysed sample.

Figure 10:
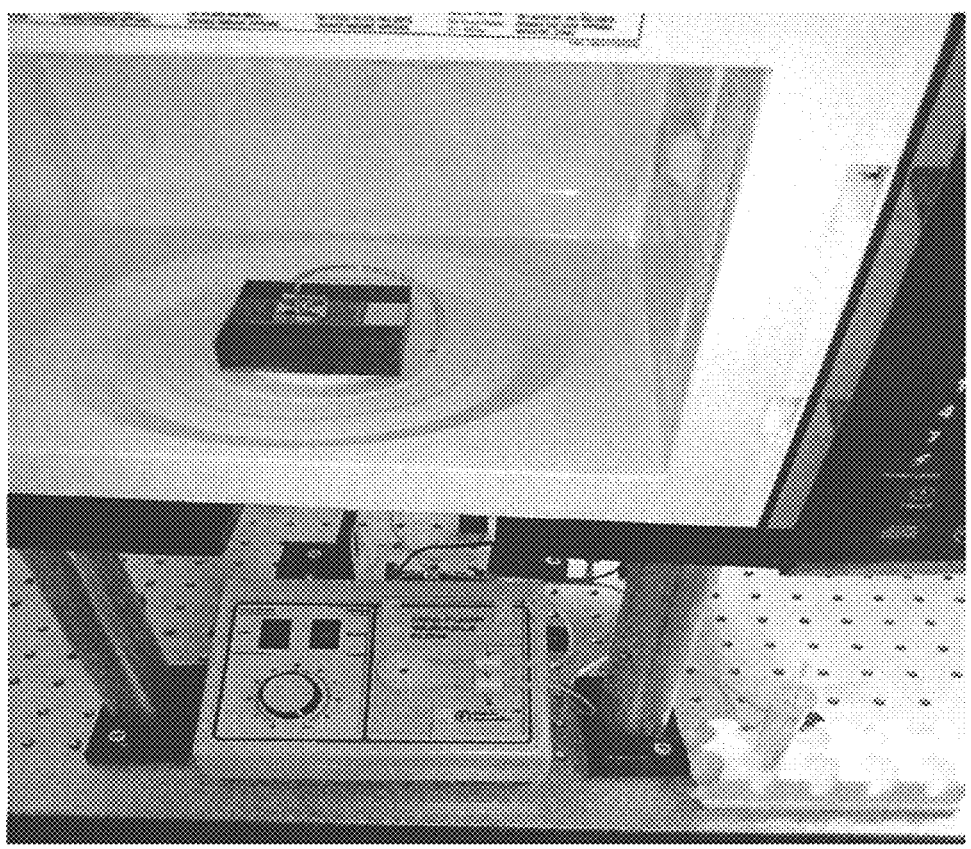
FIG. 10 shows the preferred system of FIG. 9 in a microwave chamber.

FIG. 10 shows that the flow lysing sample holder of the present invention can be mounted in a standard microwave oven, with a peristaltic pump positioned below the microwave oven. The plastic tubing, which delivers the biological material to the flow chamber, is connected to either side of the flow lysing chamber.

Figure 11:
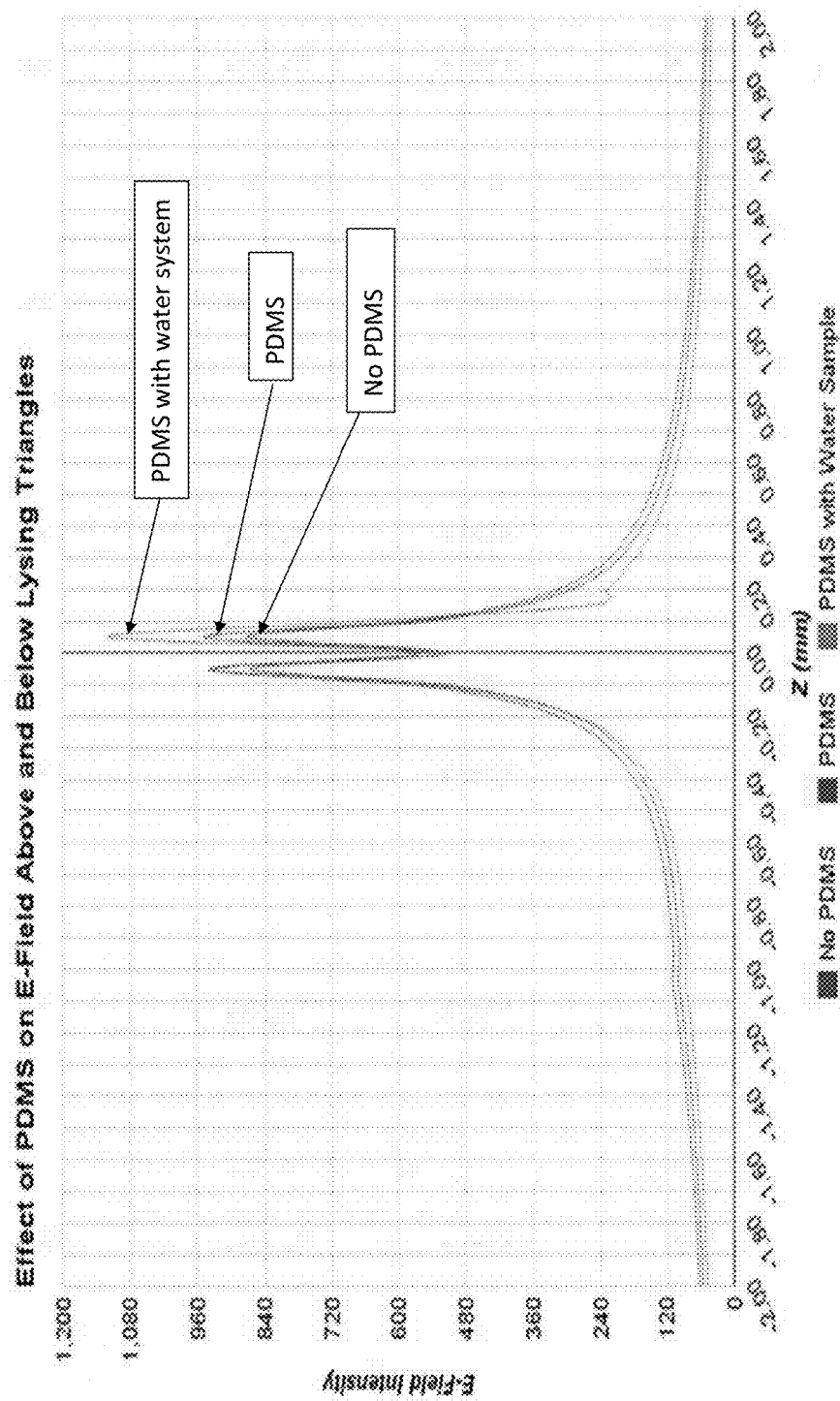
FIG. 11 shows the effect of polydimethylsiloxane polymers on E-Field above and below lysing triangles.

FIG. 11 shows that Finite Difference Time Domain (FDTD) numerical simulation can be used to optimized the channel width and the penetration of the microwaves into the lysing channel. The testing material used was polydimethylsiloxane (PDMS) and found to be more effective to increase the E-field intensity.

Figure 12:
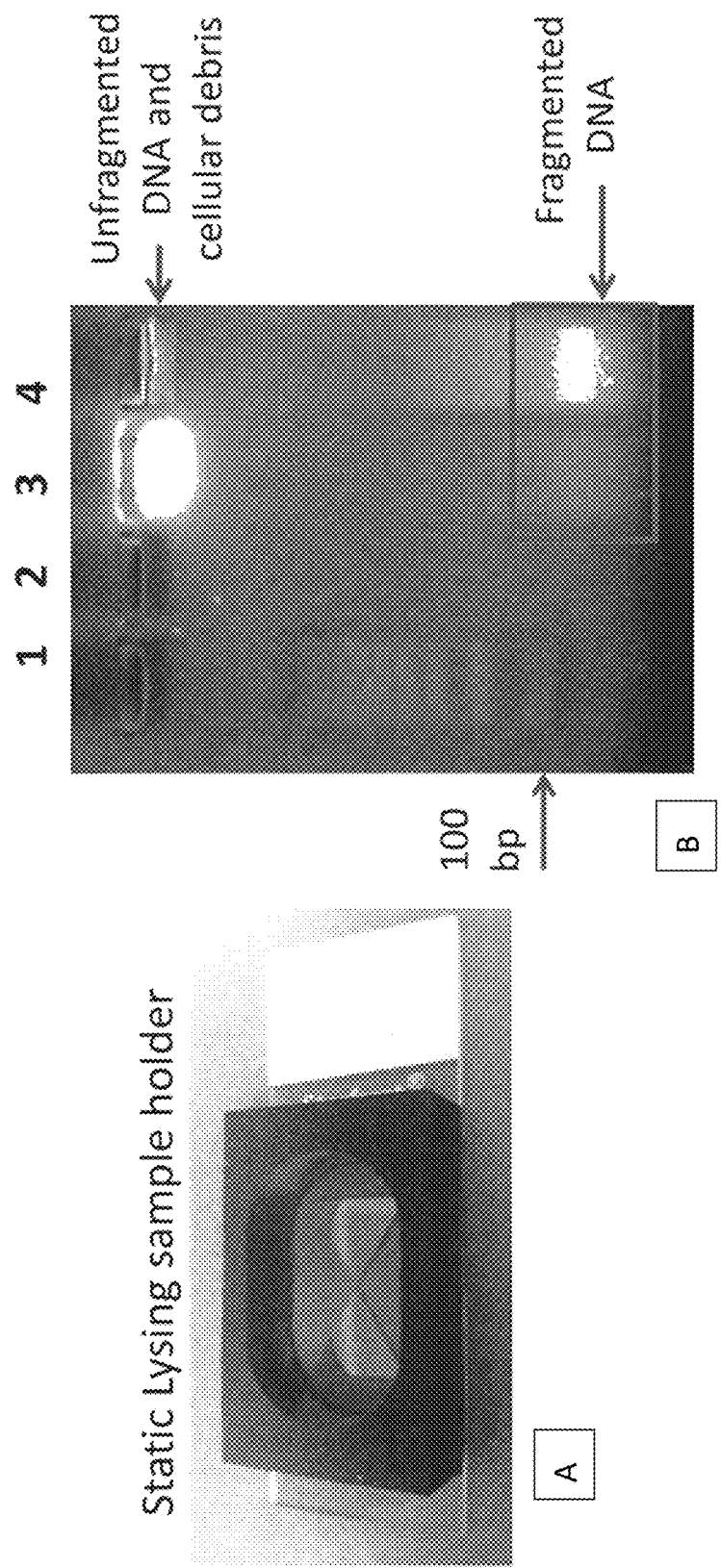
FIG. 12 shows the lysing efficiency of use of a large static lysing chamber (A) versus a flow lysing system (B) (Lane 1—DNA Ladder; Lane 2—Unlysed GC cells; Lane 3—Lysed GC—static lysing chamber; Lane 4 Lysed GC—Flow Lysing).
Figure 13:
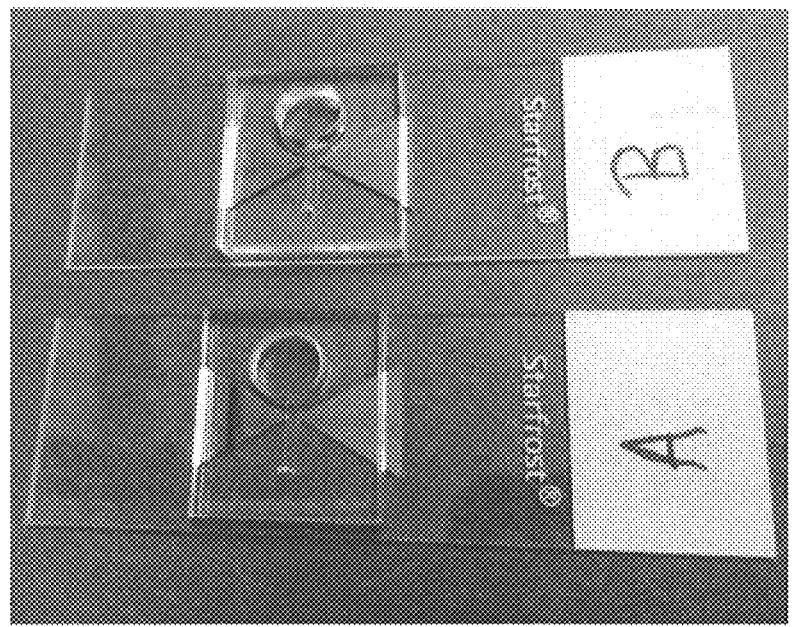
FIG. 13 shows the differences and stability of lysing triangles in both static system (i before and after) and flow lysing system (ii A and B).
Figure 13:
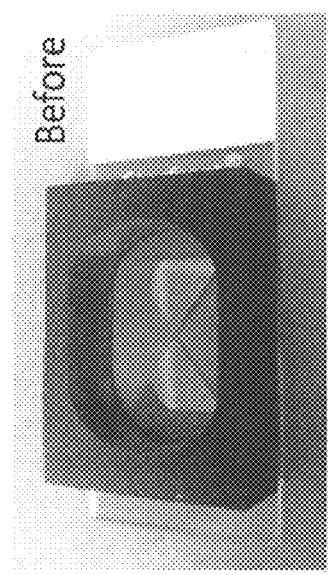
Figure 13:
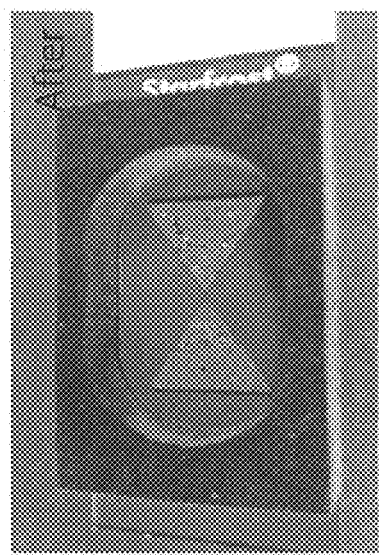

The present flow lysing system may be used in chemical, biochemical and biological applications, including to lyse (split open) bugs, microbes, algae, bacteria or viruses over a large concentration range, from 1 to $10^{12}$ cells/ml, but additionally to fragment the DNA/RNA or both into smaller pieces, both single and double stranded. FIG. 12B provides for results from electrophoresis gel showing that the lysing efficiency of *Neisseria gonorrhea* is more pronounced with the flow lysing system of FIG. 9 as compared to a single use, disposable lysing chamber of FIG. 12A. This can be seen by comparing lanes 3 (Lysed GC-static lysing chamber) and 4 (Lysed CG-flow lysing), where the *gonorrhea* DNA is much more fragmented in Lane 4, indicative of more efficient lysing. FIG. 13 (*i*) shows the static lysing triangles before and after the lysing and it is evident that the triangles are not reusable. However the flow lysing chambers in FIG. 13(*ii*) shows that the flow lysing chamber before use (A) and after use (B) and the flow chamber remains intact after several time being used (45 seconds each time).

Figure 14:
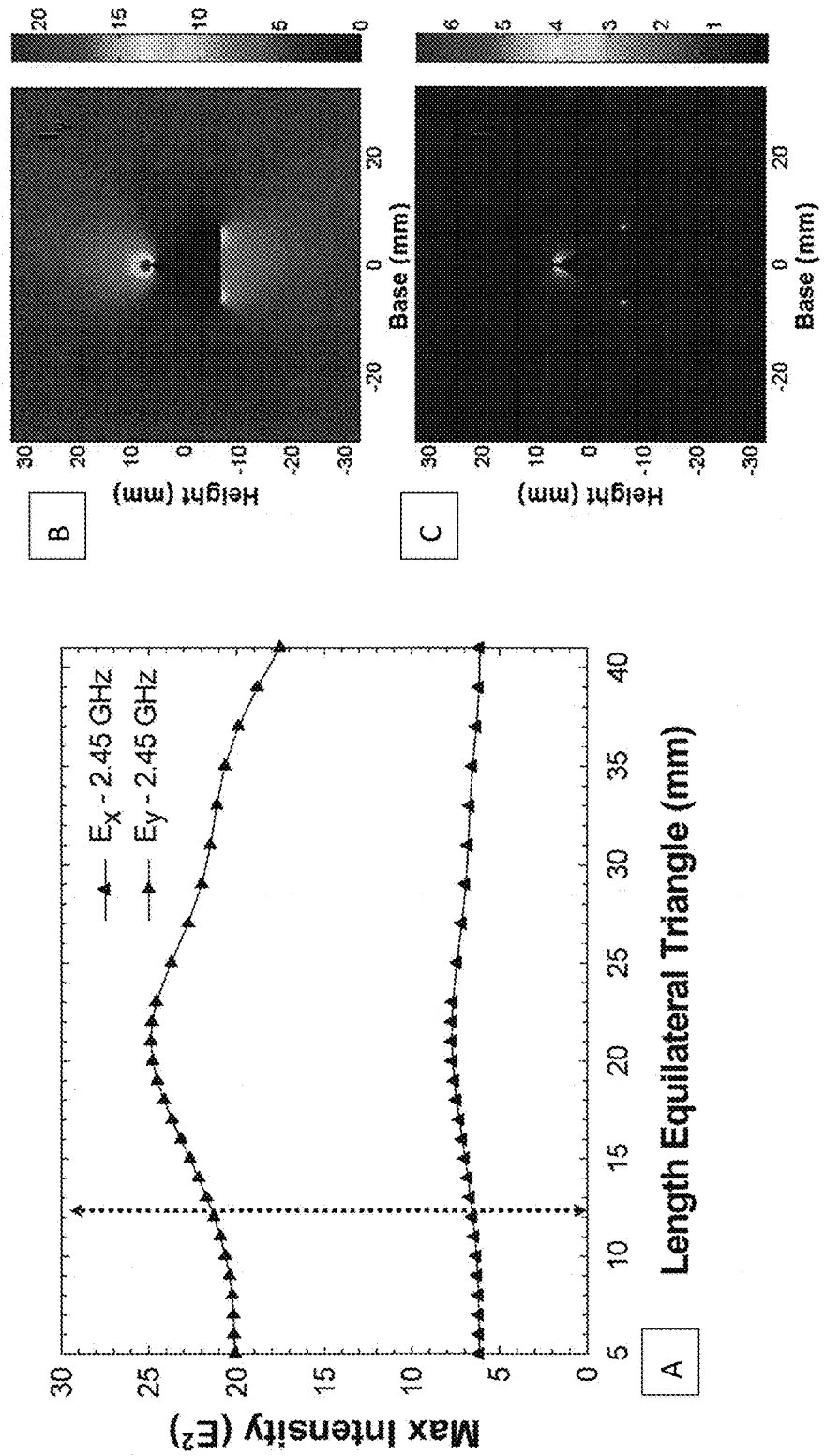
FIG. 14 shows the results of simulation for optimum triangle size for lysing, E-Field Intensity (A), (B) and (C).

FIG. 14 (A) shows simulation results of maximum intensity ($I_x$) ($E_x^2$) and $I_y$ ($E_y^2$) pixel intensities plotted versus the length of equilateral triangles. Simulated intensity, $E_x^2$ and $E_y^2$ for the electromagnetic filed distribution of 2.45 GHz microwave frequencies incident upon 2-D equilateral triangles with 12.3 mm length (dotted vertical line in (A).

Apex Shapes can be fabricated from gold, Copper, Aluminum, Silver, Platinum, Palladium, Iron, Lead, Carbon, Graphite triangles or combinations therefor (or other apex shapes) positioned anywhere from 1 µm to 5 cm apart and more preferably from about 1 mm to 12 mm. The metal apexes can be thermally evaporated, sputtered, painted (ink jet technology) or stamped onto a support. The thickness of the metal can be anywhere from 25 nanometers or 5 mm thick. Any plastic, wooden or fabric material can be used to create a channel above the apexes. Either one, or several chambers can be used, stacked on top of each other, with the liquid or gas peristaltically pumped between the apexes. This approach of using several flow lysing chambers simultaneously increases the amount of material being lysed per unit time.

Figure 15:
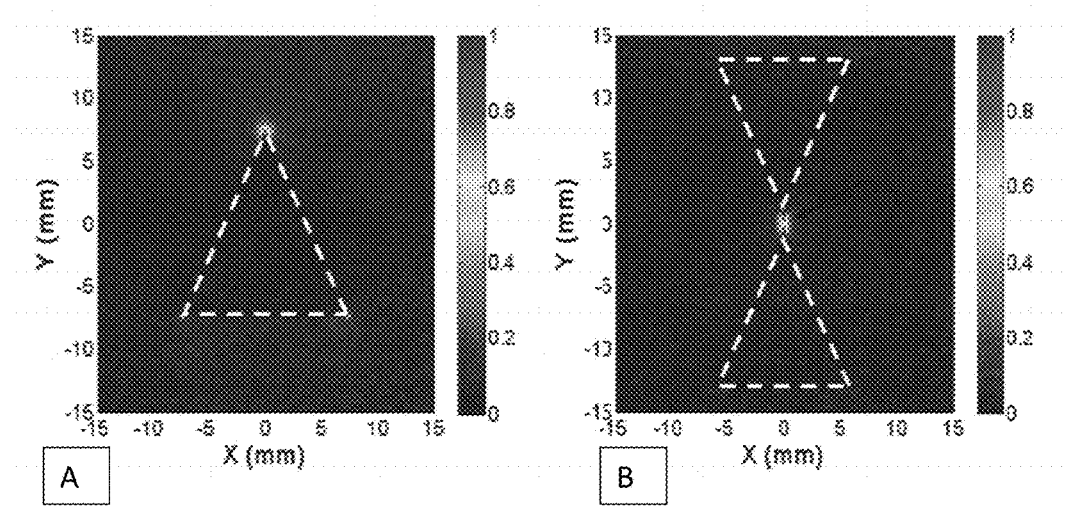
FIG. 15 shows that geometric shapes can be used to focus microwaves, single (A) and two triangles (B).
Figure 16:
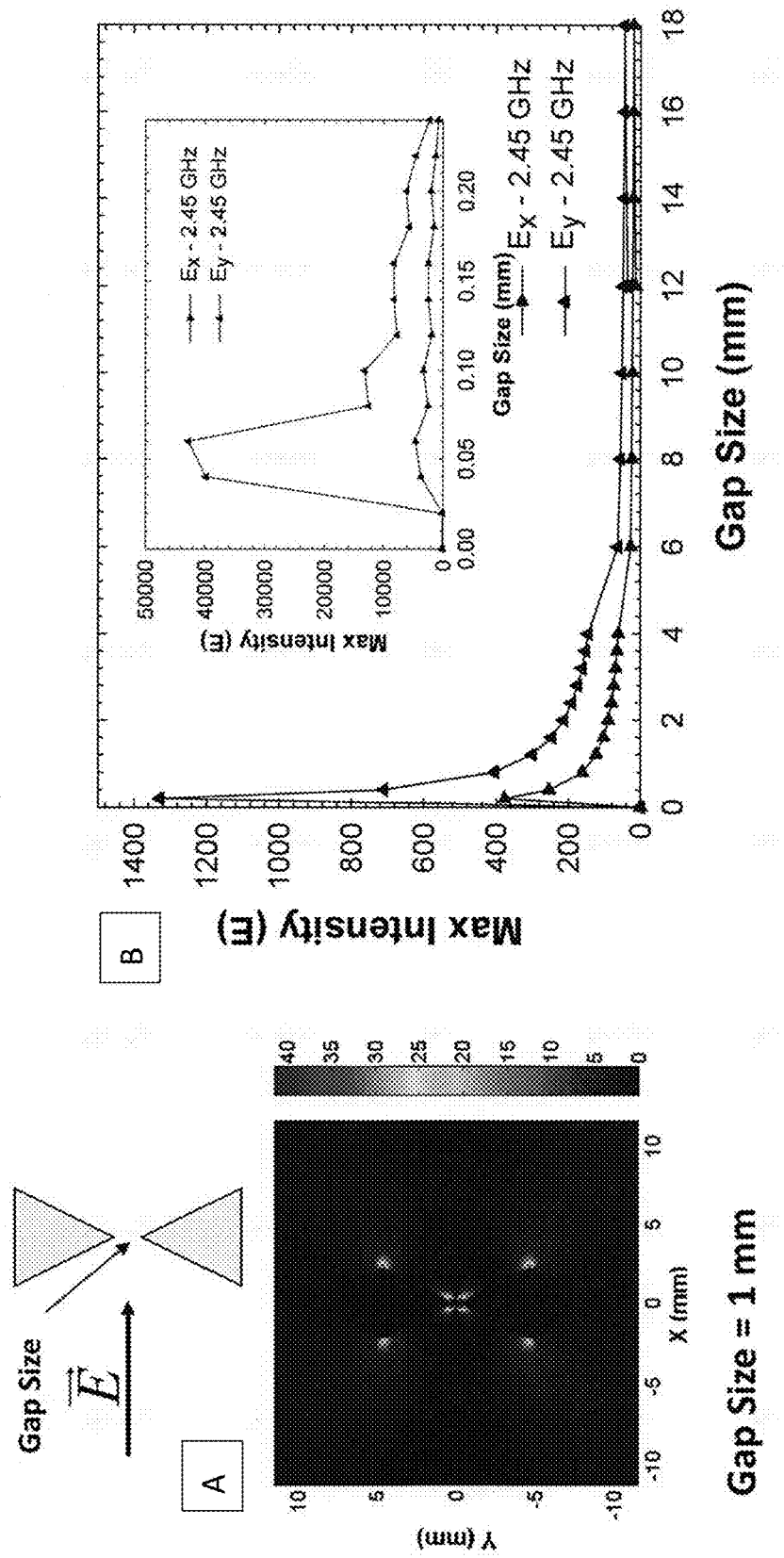
FIG. 16 shows the results of simulation for optimum gas size between the apexes of the triangles, Maximum Intensity (A) and (B).

Triangles or other shapes can be used to focus the microwaves within the microwave cavity. Two or more apexes can be used to focus the microwaves. As shown in FIG. 15, one triangle does not solely focus microwaves at a single apex but instead at all edges. However, with the bow-tie geometry the microwaves are focused at the apexes. The gap size between the triangles is critical for heating between the apexes. FIG. 16 shows that for 12.3 mm equilateral triangles, smaller gap sizes focus more stronger. Specifically, FIG. 16 shows simulated intensity images, $I_x$ (top) and $I_y$ (bottom) of the electromagnetic field distribution for 2.45 GHz microwave frequencies incident upon two 2-D equilateral triangles with 12.3 mm length and oriented with the sample geometry shown. The incident field is held constant and the gap size is varied in subsequent simulations, 1 mm (left) and 12 mm (right) gap size examples are shown.

Figure 17:
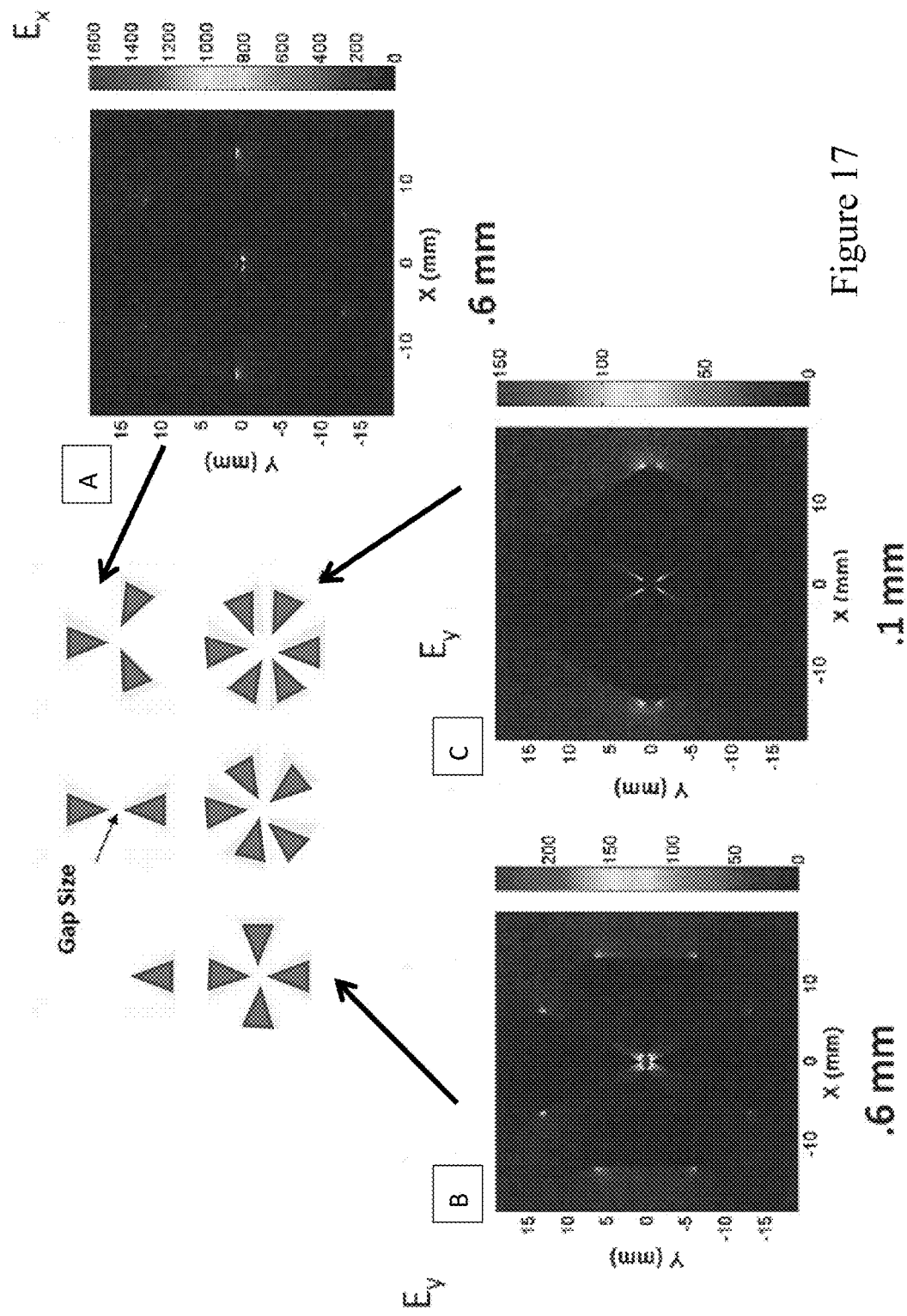
FIG. 17 shows other triangle geometries simulated for microwave focusing, three triangles (A), four triangles (B) and six triangles (C).
Figure 18:
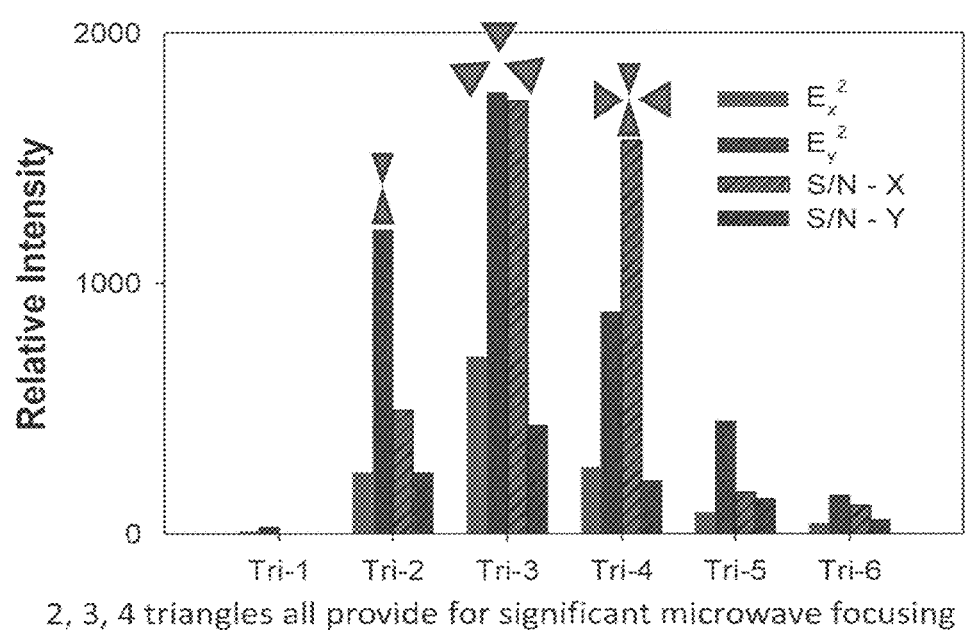
FIG. 18 shows the results for optimizing the triangular system for maximum focusing.

FIG. 17 shows multiple lysing geometries that can be used to focus microwaves for lysing, wherein the maximum fields obtained from between the triangles are for 2, 3 and 4 equally spaced triangles. For the structures shown in FIG. 18, the lysing channels can either be i) In the same plane as the triangles, or ii) into the paper, i.e. 90 degrees to the physical location of the triangles on the substrates. FIG. 18, shows plots of the relative microwave focusing intensity of various structures. 2, 3 and 4 triangles show significant ability to focus microwaves at their apexes.

Importantly, the lysing system of the present invention can be used to:

To lyse (split open) bugs, microbes, algae, bacteria or viruses, but additionally denature proteins.

To lyse (split open) bugs, microbes, algae, bacteria or viruses, but additionally to recover lipids, such as for downstream biodiesel production.

To rapidly lyse very high concentrations of bugs, microbes, algae, bacteria or viruses, over a large concentration range, from 1 to $10^{12}$ cells/ml, for applications such as lipid extraction for biodiesel production.

To rapidly lyse and subsequently study single cells, flowing through the apexes. These single cells may additionally be visualized by a microscope.

To lyse (split open) bugs, microbes, algae, bacteria or viruses, where the lysate can studied in real time, as soon as lysed, by spectroscopic techniques, such as fluorescence, absorption spectrophotometry, IR, NMR spectroscopy etc.

To rapidly lyse and subsequently study single cells, flowing through the apexes where the lysate is then flowed into a mass spectrometer for analysis.

To rapidly lyse flowing encapsulated drugs, where the drug can be intravenously injected into either an animal or patient.

To rapidly apply heat to a small volume at the apexes to initiate or enhance a chemical, biochemical or polymeric reaction, where the material (product and excess starting material) flow away after rapid heating.

REFERENCES

The contents of all cited references are incorporated by reference herein for all purposes.

1. Joshi T, Mali B, Geddes C D, Baillie L (2014) Extraction and Sensitive Detection of Toxins A and B from the human pathogen *Clostridium difficile* in 40 seconds using Microwave-Accelerated Metal-Enhanced Fluorescence. *Plos One*, 9(8), e104334.
2. Melendez J H, Huppert J S, Jett-Goheen M, Hesse E A, Quinn N, et al. (2013) Blind evaluation of the microwave-accelerated metal-enhanced fluorescence ultra-rapid and sensitive *Chlamydia trachomatis* test by use of clinical samples. *J. Clin Microbiol*, 41: 2913-2920.
3. Tennant S M, Zhang Y, Galen J E, Geddes C D, Levine M M (2011) Ultra-fast and sensitive detection of non-typhoidal *Salmonella* using microwave-accelerated metal-enhanced fluorescence ("MAMEF"). *PLoS One*. 6(4):e18700.
4. Zhang Y, Agreda P, Kelly S, Gaydos C, Geddes C D (2011) Development of a Microwave-Accelerated Metal-Enhanced Fluorescence 40 seconds, <100 cfu/ml point of care assay for the detection of *Chlamydia Trachomatis*. *IEEE Trans Biom Eng*. 58: 781-784.
5. Asian K, Previte M J R, Zhang Y, Gallagher T, Baillie L, et al. (2008). Extraction and Detection of DNA from *Bacillus Anthracis* Spores and the Vegetative Cells within 1 minute, *Anal Chem*. 80: 4125-4132. (Thermal imaging studies)
6. Asian K, Zhang Y, Hibbs S, Baillie L, Previte M J, et. al. (2007) Microwave-accelerated metal-enhanced fluorescence: application to detection of genomic and exosporium anthrax DNA in <30 seconds. *Analyst* 132: 1130-1138.
7. Asian K, Geddes, C D (2008) A review of an Ultra-Fast and Sensitive Bioassay Platform Technology: Microwave-accelerated Metal-Enhanced Fluorescence. *Plasmonics* 3: 89101
8. Asian K, Geddes C D. 2006. Microwave-Accelerated Metal-Enhanced Fluorescence (MAMEF): application to ultra-fast and sensitive clinical assays. *J Fluoresc* 16: 3-8.
9. Asian K, Malyn S N, Bector G, Geddes C D (2007). Microwave-accelerated metal-enhanced fluorescence: an ultra-fast and sensitive DNA sensing platform. *Analyst* 132:1122-1129.
10. Swanson J. (2009) Best practices in GWAS. Gen Tech. New York, N.Y. Geno
11. Yaghmaee P, Durance T D (2005) Destruction and injury of *Escherichia coli* during microwave heating under vacuum. *J Appl Microbiol* 98: 498-506.
12. Watanabe K, Kakita Y, Kashige N, Miake F, Tsukiji T (2000) Effect of ionic strength on the inactivation of micro-organisms by microwave irradiation. *Lett Appl Microbiol* 31: 52-6.
13. Kakita Y, Kashige N, Murata K, Kuroiwa A, Funatsu M, et al. (1995) Inactivation of *Lactobacillus* bacteriophage PL-1 by microwave irradiation. *Microbiol Immunol* 39: 571-6.
14. Yang Y, Hang J (2013) Fragmentation of genomic DNA using microwave irradiation. *J Biomol Tech* 24: 98-103.
15. Torrone E A, Johnson R E, Tian L H, Papp J R, Datta S D, Weinstock H S. (2013) Prevalence of *Neisseria gonorrhoeae* among persons 14 to 39 years of age, United States, 1999 to 2008. *Sex Transm Dis* 40: 202-205.
16. Maertens de Noordhout C, Devleesschauwer B, Angulo F J, Verbeke G, et al. (2014) The global burden of listeriosis: a systematic review and meta-analysis. *Lancet Infect Dis* 14: 1073-382.
17. Previte M J R, Asian K, Geddes C D (2007) Spatial and temporal control of microwave triggered chemiluminescence: a protein detection platform. *Anal Chem* 79: 7042-7052.
18. Yang S, Ramachandran P, Hardick A, Hsieh Y H, Quianzon C, Kuroki M, Hardick J, Kecojevic A, Abeygunawardena A, Zenilman J, Melendez J, Doshi V, Gaydos C, Rothman R E: Rapid PCR-Based Diagnosis of Septic Arthritis by Early Gram-Type Classification and Pathogen Identification: *J Clin Microbiol* 2008: 46, 1386-1390.
19. Rothman R, Ramachandran P, Yang S, Hardick A, Won H, Kecojevic A, Quianzon C, Gaydos C: Use of Quantitative Broad-based Polymerase Chain Reaction for Detection and Identification of Common Bacterial Pathogens in Cerebrospinal Fluid: *Acad Emerg Med* 2010: 17, 741-747.
20. Won H, Yang S, Gaydos C, Hardick J, Ramachandran P, Hsieh Y H, Kecojevic A, NjanpopLafourcade B M, Mueller J E, Tameklo T A, Badziklou K, Gessner B D, Rothman R E: A broad range assay for rapid detection and etiologic characterization of bacterial meningitis: performance testing in samples from sub-Sahara: *Diagn Microbiol Infect Dis* 2012: 74, 22-7.
21. Yang S, Rothman R E, Hardick J, Kuroki M, Hardick A, Doshi V, Ramachandran P, Gaydos C A: Rapid Polymerase Chain Reaction-based Screening Assay for Bacterial Biothreat Agents: Acad Emerg Med 2008: 15, 388-392.
22. Yang S, Lin S, Kelen G D, Quinn T C, Dick J D, Gaydos C A, Rothman R E: Quantitative Multiprobe PCR Assay for Simultaneous Detection and Identification to Species Level of Bacterial Pathogens. *J. Clin. Microbiol* 2002: 40, 3449-3454.
23. Hardick J, Won H, Jeng K, Hsieh Y H, Gaydos C A, Rothman R E, Yang S: Identification of Bacterial Pathogens in Ascitic Fluids from Patients with Suspected Spontaneous Bacterial Peritonitis by use of Broad-Range PCR (165 PCR) coupled with High-Resolution Melt Analysis. *J Clin Microbiol* 2012: 50, 2428-32.
24. Rasmussen J P, Barbez P H, Burgoyne L A, Saint C P (2008) Rapid preparation of cyanobacterial DNA for real-time PCR analysis. *Lett Appl Microbiol* 46:14-19.
25. Jadaon M M, Dashti A A, Lewis H L, Habeeb F M (2009) Whole-blood polymerase chain reaction and restriction fragment length polymorphism: a simplified method by microwave irradiation. *Med Princ Pract* 18: 280-283.
26. Woo I S, Rhee I K, Park H D (2000) Differential damage in bacterial cells by microwave radiation on the basis of cell wall structure. *Appl Environ Microbiol* 66: 2243-2247.

That which is claimed is:

1. A microfluidic system for lysing and fragmenting a biological material comprising:
   a substrate;
   at least a first and second metallic triangle positioned on the substrate wherein an apex of the first triangle is opposite an apex of second triangle to form a reaction zone positioned between the apexes of the first and second metallic triangle;
   a layer of polymeric material covering at least the first and second metallic triangles and the reaction zone;
   a source of microwave energy positioned and focused to emit microwave energy and deliver to the reaction zone an amount of microwave energy to lyse and/or fragment the biological material;
   an inlet channel recessed into the polymeric layer and communicatively connected to the reaction zone and of a sufficient size to provide flow of a solution of the biological material through the reaction zone; and
   an outlet channel or collection vessel communicatively connected to the reaction zone for collection or movement of the lysed or fragmented biological material from the reaction zone.

2. The microfluidic system of claim 1, wherein the flow of biological material through the reaction zone formed between the apexes of the first and second metallic triangles provides for non-physical contact of the flow of the biological material with the metallic triangles.

3. The microfluidic system of claim 1, wherein the biological materials comprise bacteria, viruses, yeast, algae, or any microorganism.

4. The microfluidic system of claim 1, wherein the triangles are right triangles, equilateral triangles, isosceles triangles, scalene triangles, obtuse triangles or acute triangles.

5. The microfluidic system of claim 1, wherein the triangles are equilateral triangles ranging in size from about 6 mm to 25 mm.

6. The microfluidic system of claim 5, wherein the equilateral triangles range in size from 10 mm to 16 mm.

7. The microfluidic system of claim 1, wherein the reaction zone is from about 0.05 mm to 30 mm.

8. The microfluidic system of claim 1, wherein microwave energy is delivered in power levels from about 100 watts to 600 watts.

9. The microfluidic system of claim 1, wherein microwave energy is delivered for 30 to 120 seconds.

10. The microfluidic system of claim 1, wherein the metallic triangles is fabricated from silver, gold, copper, zinc, indium, rhodium, aluminum, or platinum.

11. The microfluidic system of claim 1, wherein the system is a closed loop system wherein both the inlet and outlet channels are connected to a pumping system to provide for a continuous flow of biological material between the apexes.

12. The microfluidic system of claim 11, wherein the closed loop system captures and transports dangerous gases, side products or released biologicals before, during and after lysing.

13. The microfluidic system of claim 11, wherein the system isolates DNA or RNA from lysed bacteria, viruses, yeast, algae, or any microorganism.

14. The microfluidic system of claim 1, further comprising a pumping system to move the biological material from the inlet channel through the reactive zone and any formed lysate to a collection vessel.

15. A method for lysing and fragmenting a biological material, the method comprising:
    introducing the biological material through an inlet channel to pass through a reaction zone, wherein the reaction zone is positioned between an apex of a first metallic triangle and an apex of a second metallic triangle;
    applying and focusing microwave energy to the reaction zone in an amount to lyse and/or fragment the biological material.

16. The method of claim 15, wherein the biological materials comprise bacteria, viruses, yeast, algae, or any microorganism.

17. The method of claim 15, wherein the triangles are right triangles, equilateral triangles, isosceles triangles, scalene triangles, obtuse triangles or acute triangles.

18. The method of claim 15, wherein the triangles are equilateral triangles ranging in size from about 6 mm to 25 mm.

19. The method of claim 18, wherein the equilateral triangles range in size from 10 mm to 16 mm.

20. The method of claim 15, wherein the reaction zone is from about 0.05 mm to 30 mm.

21. The method of claim 15, wherein microwave energy is delivered in power levels from about 100 watts to 600 watts.

22. The method of claim 15, wherein microwave energy is delivered for 30 to 120 seconds.

23. The method of claim 15, wherein the metallic triangles is fabricated from silver, gold, copper, zinc, indium, rhodium, aluminum, or platinum.

24. The method of claim 15, wherein DNA or RNA is isolated from lysed bacteria, viruses, yeast, algae, or any microorganism.

25. The method of claim 15, wherein microwave energy has a frequency from about 1 GHz to about 4 GHz.

* * * * *